US007853330B2

(12) United States Patent
Bradley et al.

(10) Patent No.: US 7,853,330 B2
(45) Date of Patent: Dec. 14, 2010

(54) APPARATUS AND METHOD FOR DETERMINING THE RELATIVE POSITION AND ORIENTATION OF NEUROSTIMULATION LEADS

(75) Inventors: Kerry Bradley, Glendale, CA (US); James Thacker, Eureka, MO (US); Michael Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 372 days.

(21) Appl. No.: 11/938,490

(22) Filed: Nov. 12, 2007

(65) Prior Publication Data

US 2008/0125833 A1   May 29, 2008

Related U.S. Application Data

(63) Continuation-in-part of application No. 11/343,007, filed on Jan. 30, 2006, and a continuation of application No. 10/310,202, filed on Dec. 3, 2002, now Pat. No. 6,993,384.

(60) Provisional application No. 60/338,331, filed on Dec. 4, 2001.

(51) Int. Cl.
     *A61N 1/00* (2006.01)
(52) U.S. Cl. .............................. 607/62; 607/2; 607/117
(58) Field of Classification Search ................ 607/1, 607/28–63, 117, 2
     See application file for complete search history.

(56) References Cited

U.S. PATENT DOCUMENTS

| 3,646,940 A | 3/1972 | Timm et al. |
| 3,724,467 A | 4/1973 | Avery et al. |
| 3,822,708 A | 7/1974 | Zilber |
| 4,735,204 A | 4/1988 | Sussman et al. |
| 4,911,174 A | 3/1990 | Pederson et al. |
| 5,184,624 A | 2/1993 | Brown et al. |
| 5,201,865 A | 4/1993 | Kuehn |

(Continued)

FOREIGN PATENT DOCUMENTS

WO    WO 02/09808 A1    2/2002

OTHER PUBLICATIONS

Office Action dated Apr. 12, 2005 for U.S. Appl. No. 10/310,202, filed Dec. 3, 2002, inventor: Kerry Bradley, (6 pages).

(Continued)

*Primary Examiner*—Scott M Getzow
(74) *Attorney, Agent, or Firm*—Vista IP Law Group LLP

(57) ABSTRACT

A method for determining whether the relative position of electrodes used by a neurostimulation system has changed within a patient comprises determining the amplitude of a field potential at each of at least one of the electrodes, determining if a change in each of the determined electric field amplitudes has occurred, and analyzing the change in each of the determined electric field amplitudes to determine whether a change in the relative position of the electrodes has occurred. Another method comprises measuring a first monopolar impedance between a first electrode and a reference electrode, measuring a second monopolar impedance between second electrode and the reference electrode, measuring a bipolar impedance between the first and second electrodes, and estimating an amplitude of a field potential at the second electrode based on the first and second monopolar impedances and the bipolar impedance.

28 Claims, 18 Drawing Sheets

U.S. PATENT DOCUMENTS

| | | | |
|---|---|---|---|
| 5,333,618 | A | 8/1994 | Lekhtma et al. |
| 5,702,429 | A | 12/1997 | King |
| 5,722,402 | A | 3/1998 | Swanson et al. |
| 5,735,887 | A | 4/1998 | Barreras, Sr. et al. |
| 5,814,092 | A | 9/1998 | King |
| 5,876,336 | A * | 3/1999 | Swanson et al. ............ 600/374 |
| 5,895,416 | A | 4/1999 | Barreras, Sr. et al. |
| 5,913,882 | A | 6/1999 | King |
| 5,941,906 | A | 8/1999 | Barreras, Sr. et al. |
| 5,964,796 | A | 10/1999 | Imran |
| 6,027,456 | A | 2/2000 | Feler et al. |
| 6,038,468 | A | 3/2000 | Rex |
| 6,052,624 | A | 4/2000 | Mann |
| 6,106,460 | A * | 8/2000 | Panescu et al. .............. 600/300 |
| 6,181,969 | B1 | 1/2001 | Gord |
| 6,353,762 | B1 | 3/2002 | Baudino et al. |
| 6,393,325 | B1 | 5/2002 | Mann et al. |
| 6,516,227 | B1 | 2/2003 | Meadows et al. |
| 6,587,724 | B2 | 7/2003 | Mann |
| 6,609,029 | B1 | 8/2003 | Mann et al. |
| 6,640,119 | B1 | 10/2003 | Budd et al. |
| 6,662,053 | B2 | 12/2003 | Borkan |
| 6,741,892 | B1 | 5/2004 | Meadows et al. |
| 6,913,763 | B2 | 7/2005 | Lerner |
| 6,993,384 | B2 | 1/2006 | Bradley |
| 2003/0139781 | A1 | 7/2003 | Bradley et al. |
| 2004/0049235 | A1 | 3/2004 | Deno et al. |
| 2004/0078067 | A1 | 4/2004 | Thompson et al. |
| 2004/0082978 | A1 | 4/2004 | Harrison et al. |
| 2004/0116978 | A1 | 6/2004 | Bradley |
| 2004/0172083 | A1 | 9/2004 | Penner |
| 2006/0122653 | A1 | 6/2006 | Bradley et al. |
| 2006/0122654 | A1 | 6/2006 | Bradley et al. |

OTHER PUBLICATIONS

Office Action dated Nov. 6, 2008 for U.S. Appl. No. 11/343,007, filed Jan. 30, 2006, inventor: Kerry Bradley, (12 pages).

Office Action dated Nov. 14, 2008 for U.S. Appl. No. 11/342,989, filed Jan. 30, 2006, inventor: Kerry Bradley, (14 pages).

Office Action dated May 14, 2009 for U.S. Appl. No. 11/342,989, filed Jan. 30, 2006, inventor: Kerry Bradley, (8 pages).

Final Office Action dated Jun. 12, 2009 in U.S. Appl. No. 11/343,007, filed Jan. 30, 2006, inventor: Kerry Bradley, (11 pages).

Office Action dated Aug. 7, 2009 in U.S. Appl. No. 11/343,007, filed Jan. 30, 2006, inventor: Kerry Bradley, (7 pages).

Advisory Action dated Aug. 7, 2009 in U.S. Appl. No. 11/342,989, filed Jan. 30, 2006, inventor: Kerry Bradley, (3 pages).

\* cited by examiner

| IMPEDANCE VECTOR | DISTANCE IMPEDANCE |
|---|---|
| BI_e1E5 | 300.3 |
| BI_e1E6 | 276.1 |
| BI_e1E7 | 87.8 |
| BI_e1E8 | 246.8 |
| BI_e2E5 | 301.8 |
| BI_e2E6 | 300 |
| BI_e2E7 | 217.3 |
| BI_e2E8 | 84.1 |
| BI_e3E5 | 342.5 |
| BI_e3E6 | 339.6 |
| BI_e3E7 | 290.4 |
| BI_e3E8 | 278.7 |
| BI_e4E5 | 327.3 |
| BI_e4E6 | 332.6 |
| BI_e4E7 | 289.4 |
| BI_e4E8 | 291.3 |

APPARATUS AND METHOD FOR DETERMINING THE RELATIVE POSITION AND ORIENTATION OF NEUROSTIMULATION LEADS

RELATED APPLICATIONS

The present application is a continuation-in-part of U.S. patent application Ser. No. 11/343,007, filed Jan. 30, 2006, which is a continuation of U.S. patent application Ser. No. 10/310,202, filed Dec. 3, 2002 (now U.S. Pat. No. 6,993,384), which application claims the benefit of U.S. Provisional Patent Application Ser. No. 60/338,331, filed Dec. 4, 2001, each of which is incorporated herein by reference.

BACKGROUND OF THE INVENTION

The present invention relates to neurostimulation systems, such as a spinal cord stimulation (SCS) system, and more particularly to a method for determining the relative position and orientation of electrodes on a neurostimulation lead or leads used with such a system.

In SCS systems, positioning of the leads is critical to the success of the therapy. During surgery, the physician places the leads in a very careful manner in order to locate the electrodes proximal to neural elements that are the target of the stimulation. During and after placement, stimulation energy is delivered to verify that the leads are indeed stimulating the appropriate neural elements.

However, if the leads happen to shift position, the targeted neural elements may no longer be appropriately stimulated. At best, this can require electrical reprogramming to restore therapy or, at worst, surgical revision, where a second surgery is required and the leads must be manually readjusted. In the first case, the physician may have only a suspicion that a lead has shifted position, based on patient reporting of paresthesia, which is not foolproof. Also, attempting to reprogram the leads based on paresthesia locations can be challenging.

What is needed is a more objective technique for verifying the position of the leads.

Prior art approaches for determining the lead position are disclosed in U.S. Pat. Nos. 4,486,835; 4,539,640; and 5,184,624, which patents are incorporated herein by reference.

SUMMARY OF THE INVENTION

The present invention addresses the above and other needs by providing a cross-check technique for verifying the position of the electrodes of the implanted leads. A first technique involves the use of interelectrode impedance. A second technique involves measured field potentials. A third technique involves estimated field potentials. Any of these techniques advantageously allows the relative orientation of one electrode on an implanted lead to other electrodes on the implanted lead or adjacent implanted leads in the spinal column or other body/tissue location to be readily determined. Such techniques are useful not only for reprogramming, but also to estimate if the shifted orientation of the electrodes is sufficiently large so as to make electrical reprogramming a waste of time, thereby suggesting that surgery may need to be performed for repositioning.

At present, the correct lead position may only be determined by X-ray or fluoroscopy. Disadvantageously, X-ray and fluoroscopy require expensive equipment, significant time, and appropriate medical facilities, most of which are not readily available. The general process for fitting a neurostimulation patient, i.e., a spinal cord stimulation patient, is described, e.g., in U.S. Pat. Nos. 6,052,624; 6,393,325; in published international patent application WO 02/09808 A1 (published 7 Feb. 2002); and in U.S. patent application (assigned to the same assignee as the present application) Ser. No. 09/626,010, filed Jul. 26, 2000; and Ser. No. 09/740,339, filed Dec. 18, 2000, which patents, publication, and applications are incorporated herein by reference.

As indicated in those documents, prior to fitting a patient with the certain types of neurostimulation leads, the relative orientation of the electrodes on the implanted leads should be known in order to allow appropriate navigation of the stimulation energy. At present, a determination of the relative orientation typically requires that a fluoroscope or X-ray image of the implanted leads be present at the time of patient setup with the system programmer. Disadvantageously, however, such images may not always be available. Moreover, between the time of implant and follow-up visits, the leads may have shifted and the fluoroscope image may no longer be valid. This can result in poor patient outcomes due to inappropriate or unexpected stimulation effects during fitting.

Hence, it is seen that there is a need for the cross-check techniques provided by the present invention, which techniques can be used to verify the position of the leads at numerous times during the lifetime of the implanted leads, e.g., during initial implantation and programming, during follow-up visits, throughout the trial period, and during subsequent reprogramming sessions.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG), radio frequency (RF) transmitter, or similar electrical stimulator, that may be used as a component of numerous different types of stimulation systems. The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, a peripheral nerve stimulator, or in any other neural stimulator configured to treat urinary incontinence, sleep apnea, shoulder sublaxation, etc.

The embodiments described herein use: (1) interelectrode impedance; (2) actual field potentials; or (3) estimated field potentials to determine the relative orientation of one electrode on an implanted lead to other electrodes on the implanted lead or adjacent implanted leads in the spinal column or other body/tissue location.

Figure 1:
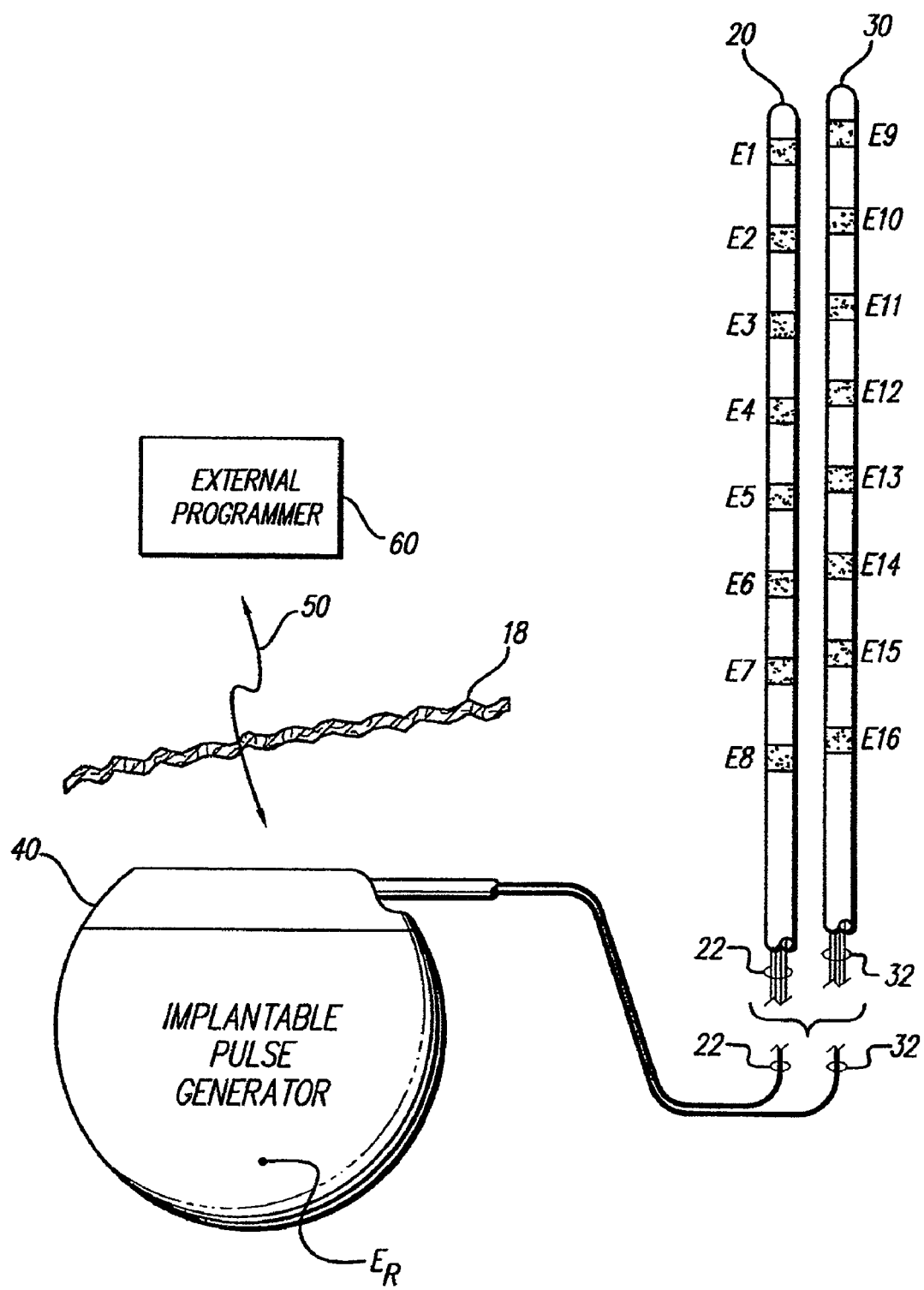
FIG. 1 illustrates a neurostimulation system wherein two leads, each having eight in-line electrodes thereon, are positioned side-by-side, and wherein each lead is connected to an implantable pulse generator (IPG), which IPG is, in turn, coupled to an external programmer.

Before describing the three techniques, any of which may be used, it will be helpful to first briefly provide an overview of a representative neurostimulation system of the type in which these techniques may be used. A representative neurostimulation system is illustrated in FIG. 1. Such system may include a first implantable lead 20 and a second implantable lead 30. Each lead includes a series of in-line electrodes thereon. For the example shown in FIG. 1, the first lead 20 contains eight in-line electrodes E1, E2, E3, . . . E8. The second lead 30 also contains eight in-line electrodes E9, E10, E11, . . . E16.

Each of the electrodes of each lead 20 or 30 are electrically connected through respective wires, embedded or carried within a body of the lead, to an implantable pulse generator (IPG) 40. The wires connected to the electrodes E1, E2, E3, . . . E8 of lead 20, for example, may be characterized as a bundle of wires 22 that are electrically connected with the IPG 40. Similarly, the wires connected to the electrodes E9, E10, E11, . . . E16 of lead 30 may be characterized as a bundle of wires 32 that are electrically connected with the IPG 40. Through these wires, carried within the respective leads 20 or 30, the IPG is able to direct electrical stimulation to selected electrodes of each lead.

When a given electrode is selected to receive an electrical stimulus, it is (for purposes of the present invention) said to be "activated". When an electrode is not selected to receive an electrical stimulus, it is said to be "non-activated". Electrical stimulation must always occur between two or more electrodes (so that the electrical current associated with the stimulus has a path from the IPG to the tissue to be stimulated, and a return path from the tissue to the IPG). The case of the IPG may function, in some modes of operation, as a return electrode $E_R$. Monopolar stimulation occurs when a selected one or more of the electrodes of one of the leads 20 or 30 is activated with a common polarity (anode or cathode), and the return electrode $E_R$ is activated at the opposite polarity. Bipolar stimulation occurs when two of the electrodes of the leads 20 or 30 are activated, e.g., when electrode E3 of lead 20 is activated as an anode at the same time that electrode E11 of lead 30 is activated as a cathode. Tripolar stimulation occurs when three of the electrodes of the leads 20 or 30 are activated, e.g., when electrodes E4 and E5 of lead 20 are activated as an anode at the same time that electrode E13 of lead 30 is activated as a cathode. In general, multipolar stimulation occurs when multiple electrodes of the leads 20 or 30 are activated, but the IPG case is not used as a return electrode.

The IPG 40 is typically programmed, or controlled, through the use of an external (non-implanted) programmer 60. The external programmer 60 is coupled to the IPG 40 through a suitable communications link, represented in FIG. 1 by the wavy arrow 50. Such link 50 passes through the skin 18 of the patient. Representative links that may be used to couple the programmer 60 with the IPG 40 include a radio frequency (RF) link, an inductive link, an optical link, or a magnetic link. The programmer 60, or other similar external device, may also be used to couple power into the IPG for the purpose of operating the IPG or charging a replenishable power source, e.g., a rechargeable battery, within the IPG. Once the IPG 40 has been programmed, and its power source has been fully charged or replenished, it may operate as programmed without the need for the external programmer 60 to be present.

Figure 2:
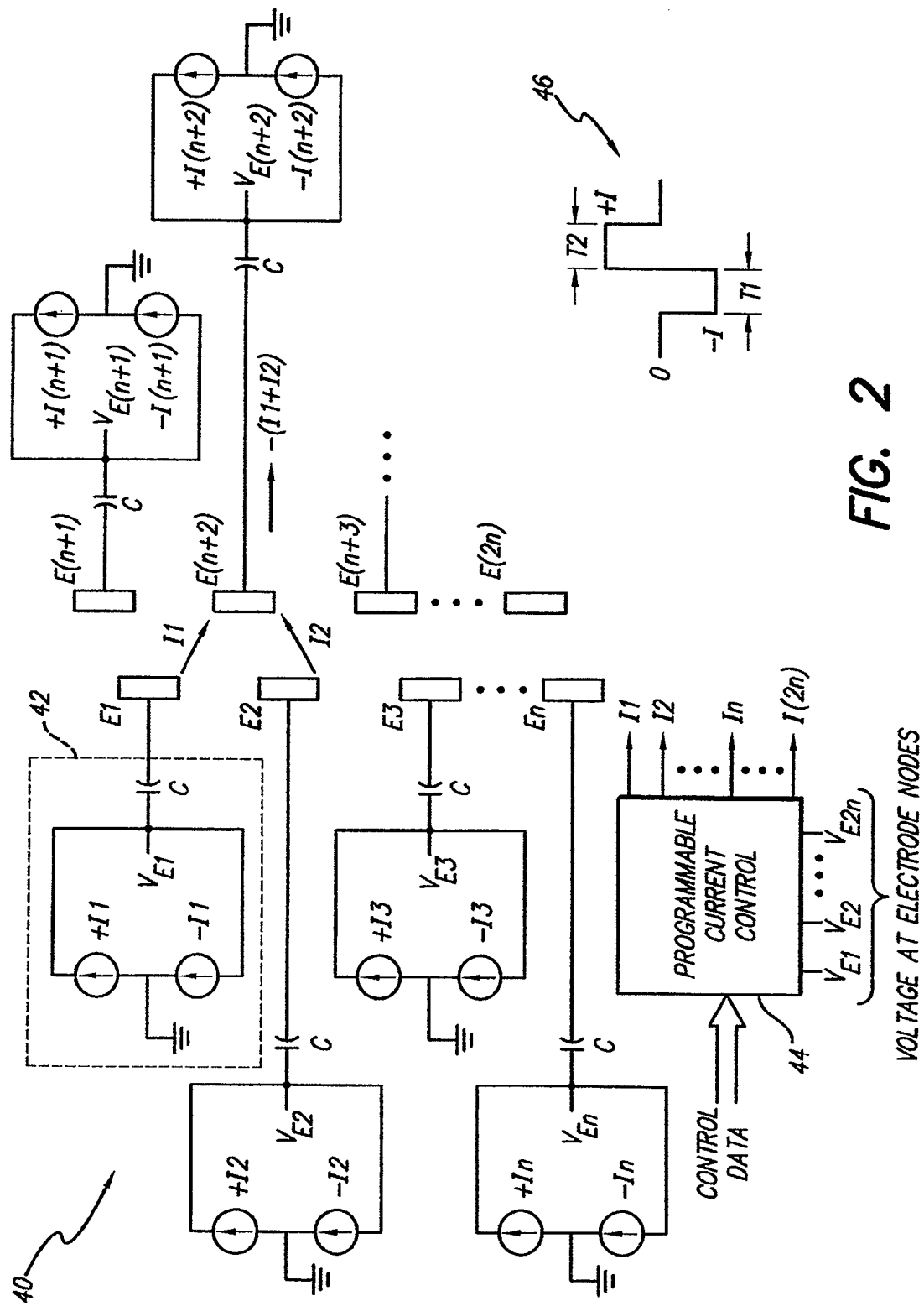
FIG. 2 shows a functional block diagram of an IPG that uses multiple programmable current sources to activate selected electrodes of the neurostimulation leads.

Turning next to FIG. 2, there is shown a representative functional block diagram of one type of IPG 40 that may be used with a neurostimulation system. As seen in FIG. 2, the IPG 40 therein depicted is made up of a multiplicity of dual current sources 42. Each dual current source 42 includes a positive current source, i.e., a current source that can function as an anode to "source" current to a load, and a current source that can function as a cathode to "sink" current from a load through the same node. The "load" is the tissue that resides between the two or more activated electrodes, and includes the wire (or other conductive element) and a coupling capacitor C that connects the electrode to the common node of the dual current source.

Thus, for example, and as depicted in FIG. 2, a first dual current source connected to electrode E1 of a first lead through a coupling capacitor C, may be programmed to produce a current of +I1 or −I1 through electrode E1, depending upon whether such dual current source is configured to operate as a cathode or an anode, when such first dual current source is turned on or enabled. Similarly, a second current source, connected to electrode E2, when turned on or enabled, may be programmed to produce a current of +I2 or −I2 through electrode E2. In a similar manner, a third current source, when enabled, may be programmed to produce a current of +I3 or −I3 through electrode E3. An nth current source, where n represents the number of electrodes on the first lead, is similarly connected to electrode En, and may be programmed to produce a current of +In or −In through electrode En when turned on or enabled.

If a second lead, also having n electrodes, is positioned adjacent the first lead, each electrode is similarly connected to a dual current source. For example, electrode E(n+1) is connected to a dual current source that produces a current of +I(n+1) or −I(n+1) through electrode E(n+1) when such (n+1)th current source is enabled. In like manner, all of the electrodes of the second lead are connected to respective dual current sources. There are thus 2n dual current sources that are respectively connected to each of the 2n electrodes of the first and second leads (n electrodes on each lead). Alternative embodiments (not shown) may employ less than 2n dual current sources connected to 2n electrodes through a suitable multiplexer circuit.

A programmable current control circuit 44 is also provided within the IPG 40 that controls, i.e., turns on or enables, at specified times, a selected current source to operate as either a cathode or an anode to source or sink a current having a desired amplitude. The control circuit 44 also disables, or turns off, selected current sources, as controlled by programmed control data received from the external programmer, or otherwise resident within the IPG. The control circuit 44 further includes the ability to measure the electrode voltage, $E_{V1}, E_{V2}, E_{V3}, \ldots E_{Vn}, \ldots E_{V(2n)}$, appearing at the output of each dual current source 42, whether the electrode is activated or non-activated. This effectively allows the electrode voltage, or electric field at the electrode, to be measured, which in turn facilitates impedance or field potential measurements to be made, which measurements are used in carrying out various steps of the invention as described below.

Thus, in operation, and as illustrated in FIG. 2, current control circuit 44 may turn on current sources +I1 and +I2 at the same time, i.e., during a time period T1, that current source −I(n+2) is turned on. All other current sources are turned off, or disabled, during the time T1. Such action causes electrodes E1 and E2 to be activated as anodes at the same time that electrode E(n+2) is activated as a cathode. That is, a current +I1 is "sourced" from electrode E1 and a current +I2 is "sourced" from electrode E2 at the same time that a current −I(n+2) is "sunk" into electrode E(n+2). The amplitudes of the currents +I1 and +I2 may be any programmed values, and the amplitude of the current −I(n+2) should be equal to −(I1+I2). That is, the current that is sourced is equal to the current that is sunk.

After the time period T1, it is common to switch the polarities of the electrodes during a second time period T2. During T2, the electrodes E1 and E2 are activated as cathodes, so that they both sink current, and electrode E(n+2) is activated as an anode, so that it sources a current equal in amplitude to the current that is sunk by electrodes E1 and E2. In this manner, a biphasic stimulation pulse 46 is produced that is characterized by a first pulse (during time period T1) of one polarity, followed by a second pulse immediately or shortly thereafter (during time period T2) of the opposite polarity. The electrical charge associated with the first pulse is made so that it is equal to the charge associated with the second pulse, thereby maintaining charge balance during the stimulation. Maintaining charge balance when stimulating living tissue is generally considered an important component of a stimulation regime. Charge balance is commonly achieved in a biphasic pulse 46 by making the amplitude of the first pulse during time T1 equal to the amplitude of the second pulse during time period T2, where T1 equals T2. However, charge balance may also be achieved using other combinations of pulse duration and amplitude, e.g., by making the amplitude of the second pulse equal to ½ the amplitude of the first pulse, while making the time period T2 equal to twice the time period T1.

Figure 3:
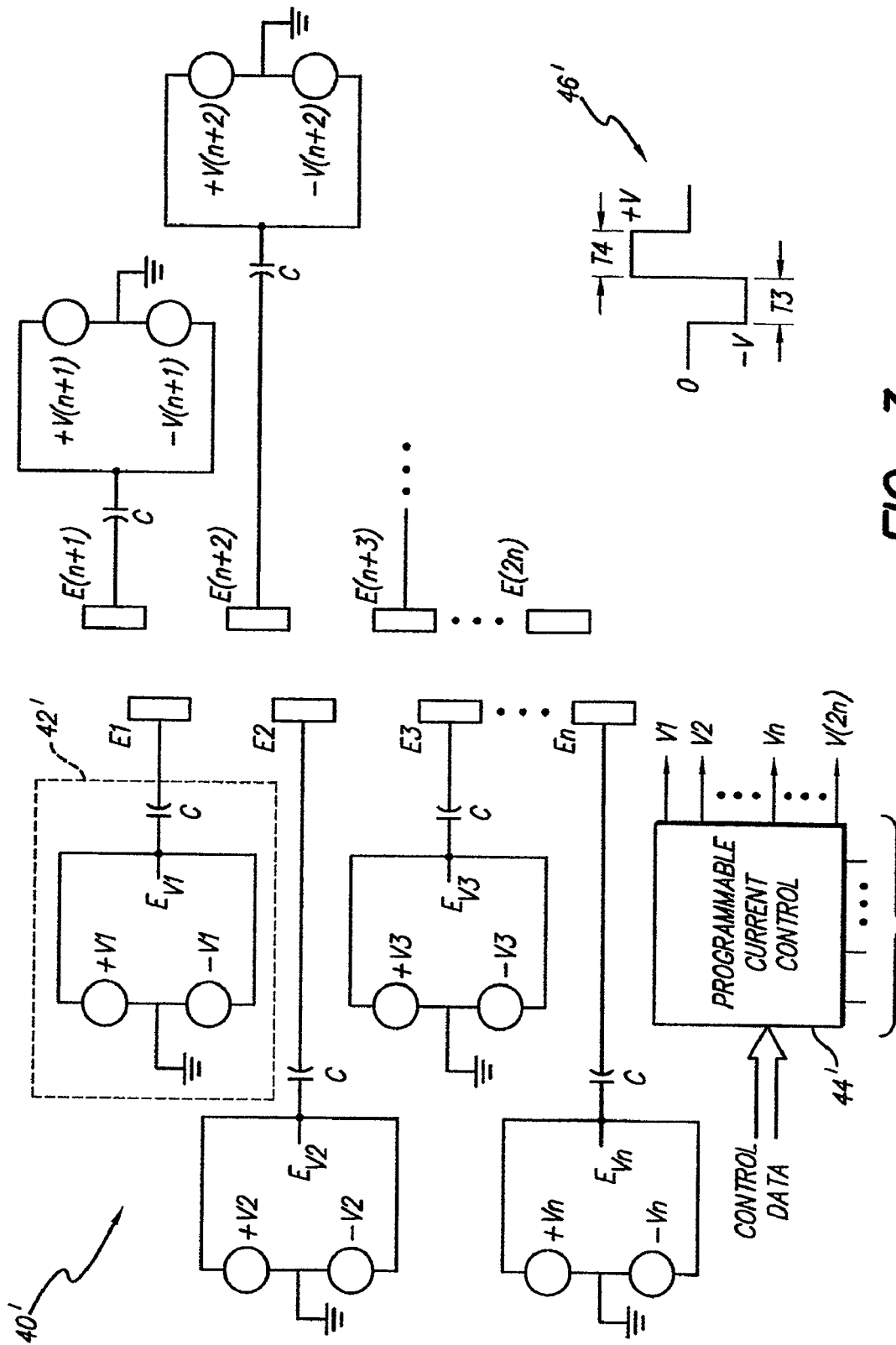
FIG. 3 shows a functional block diagram of an IPG that uses multiple programmable voltage sources to activate selected electrodes of the neurostimulation leads.

Next, with respect to FIG. 3, a functional block diagram of another type of IPG 40' that may be used in a neurostimulation system is shown. The IPG 40' shown in FIG. 3, includes a multiplicity of dual voltage sources 42', each being connected to one of the electrodes E1, E2, E3, . . . En, of a first lead, or to one of the electrodes E(n+1), E(n+2), . . . E(2n), of a second lead. Each dual voltage source 42' applies a programmed voltage, of one polarity or another, to its respective electrode, when enabled or turned on. For the configuration shown in FIG. 3, a separate dual voltage source 42' is connected to each electrode node through a coupling capacitor C. Other embodiments, not shown, may use one or two or more voltage sources that are selectively connected to each electrode node through a multiplexer circuit.

The control circuit 44', or other circuitry within the IPG 40', further includes the ability to measure the electrode current, $E_{I1}, E_{I2}, E_{I3}, \ldots E_{In}, \ldots E_{I(2n)}$, flowing to or from its respective electrode, whether the electrode is activated or non-activated, and the electrode voltage, $E_{V1}, E_{V2}, E_{V3}, \ldots E_{Vn}, \ldots E_{V(2n)}$, appearing at the output of each non-activated dual voltage source 42'. These measurements facilitate impedance and electric field measurements or calculations to be made, which measurements are used in carrying out various steps of the invention as described below.

A programmable voltage control circuit 44' controls each of the dual voltage sources 42', specifying the amplitude, polarity, and duration of the voltage that is applied to its respective terminal. Typically, stimulation is achieved by applying a biphasic stimulation pulse 46' to the selected electrodes, wherein a voltage of a first polarity and amplitude is applied during time period T3, followed by a voltage of the opposite polarity and amplitude during time period T4. The biphasic stimulation pulse 46' may be applied between any two or more electrodes.

It should be noted that the functional block diagrams of FIGS. 2 and 3 are functional diagrams only, and are not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure the voltage, or the current, flowing through an activated or non-activated electrode. Such measurements allow impedance to be determined (used with a first embodiment of the invention), allow field potentials to be measured (used with a second embodiment of the invention), or allow field potentials to be estimated (used with a third embodiment of the invention), as described in more detail below. A preferred IPG is described in international patent application WO 02/09808 A1 (published 7 Feb. 2002); and in U.S. patent application Ser. No. 09/626,010, filed Jul. 26, 2000, which publication and application have been previously referenced and are incorporated herein by reference.

With the descriptions of FIGS. 1-3 thus providing background information relative to a neurostimulation system, the embodiments will next be described. As has been indicated, the embodiments address the problem of determining the relative position between electrodes once the leads on which the electrodes are carried have been implanted. The embodiments use: (1) interelectrode impedances; (2) actual field potentials; or (3) estimated field potentials to determine the relative orientation of one electrode on an implanted lead to other electrodes on the implanted lead or adjacent implanted leads in the spinal column or other body/tissue location.

First, the interelectrode impedance technique for determining relative electrode positions for multipolar leads of a neurostimulation system will be explained in connection with FIGS. 4-6. The interelectrode impedance technique is performed by measuring impedance vectors. A vector is defined as an impedance value measured between two electrodes in the body. The value of the impedance vector is due primarily to two physical entities: (1) the electrode-electrolyte interface; and (2) the bulk impedance between the electrodes. The impedance tomography technique of the present invention relies upon the latter of the above two physical entities, i.e., upon the bulk impedance between the electrodes. The bulk impedance portion of the impedance vector may be further broken up into two contributing factors: (a) the impedance of the tissue adjacent to the electrodes; and (b) the impedance of the tissue between the electrodes.

The first factor (part a) makes up the majority of the measurement, due to the higher and non-uniform current densities near the electrode surface. However, the second factor (part b), where the current density is more uniform, has a roughly linear relationship to distance between the two electrodes, due to the definition of resistance. Resistance, R, is defined as R=(resistivity)×(distance)/cross-sectional area. The second factor (part b) is used by the interelectrode impedance technique embodiment of the invention to determine the relative spacing between electrodes and to determine the relative orientation of the leads.

By way of example, one first-order, simple embodiment of the invention is as follows: if two multipolar leads are placed in the spinal column, see FIG. 5, each having four electrodes (the electrodes of one lead being designated as e1, e2, e3, and e4; and the electrodes of the other lead being designated as E5, E6, E7 and E8), their relative orientation may be inferred by making the following measurements: (1) monopolar impedances for all electrodes; and (2) bipolar impedances between a given electrode and each electrode (one at a time) on opposing leads.

The monopolar impedances are used to "correct" the bipolar impedances for the first factor of bulk impedance, the strongly-weighted impedance near the electrode. The corrected bipolar impedances are then used to develop an impedance "map" between the electrodes. This map reveals the relative orientation of the leads. To illustrate, a sample correction formula is as follows: (distance between two electrodes e1 & e2)≈(measured bipolar impedance between two electrodes e1 & e2)+(2*offset)−(monopolar Z for electrode e1)−(monopolar Z for electrode e2), where offset=an estimate of the impedance in the monopolar impedance measurement that is NOT due to the tissue near the electrode.

After the bipolar impedances are corrected by the above formula, the relative orientation of the leads may be inferred by the relative minima of the impedance values. Where the corrected bipolar impedance between two electrodes is a minimum relative to other electrodes on an opposing array, those electrodes are relatively adjacent. This information may then be loaded into a programmer, which can then provide a graphic display of the assumed relative lead positions. Such data and/or display might then be compared with previously measured or entered and stored graphics, indicating earlier orientations. Such comparison can thus help the physician/clinician to track the lead orientation to determine appropriate programming, reprogramming, or need for surgical revision. Also, for some programming systems, the present invention may be used to automatically setup the appropriate navigation tables for steering multiple lead systems.

Figures 4, 5:
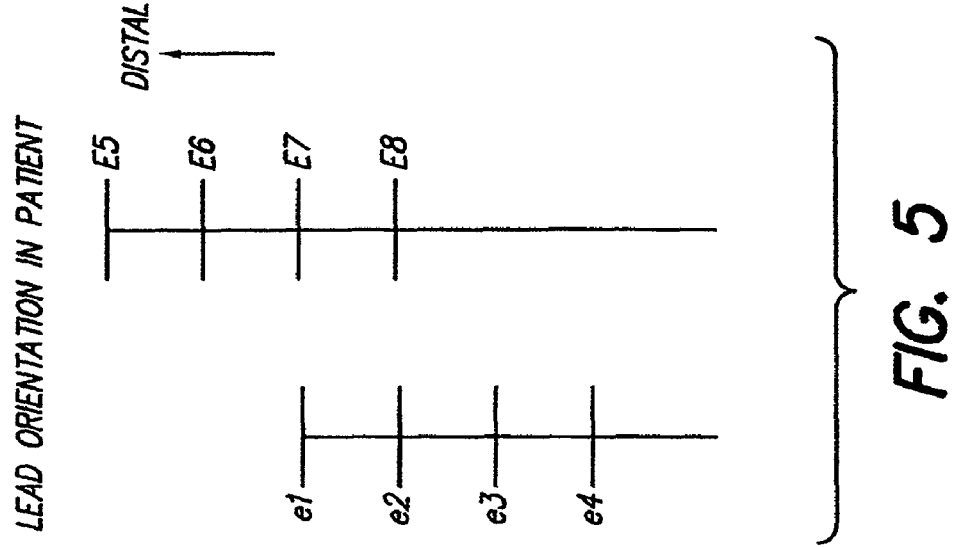
FIG. 4 is a table that contains impedance vector and distance impedance data in accordance with one embodiment of the invention.
FIG. 5 illustrates representative relative electrode orientation in a patient having dual quadrapolar leads (two side-by-side leads, each having four in-line electrodes thereon)
Figure 6:
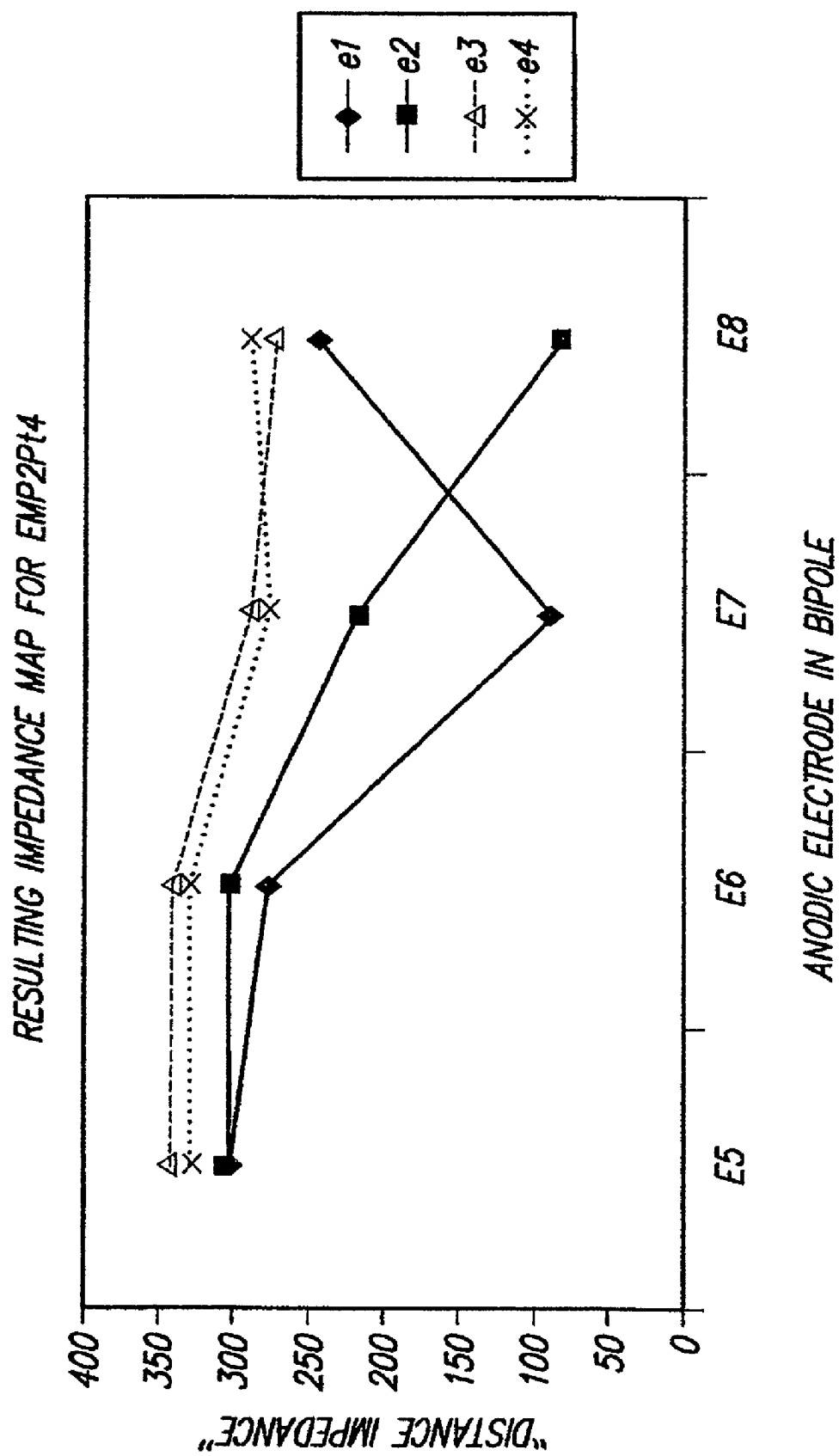
FIG. 6 is an impedance map that illustrates application of one embodiment of the invention to the electrode orientation shown in FIG. 5.

FIG. 4 illustrates data showing this simple embodiment applied to data from a patient with dual quadrapolar leads, which leads are oriented as depicted in FIG. 5. FIG. 6 shows the impedance map resulting from the measurements of FIG. 4. It can be seen that the impedance maps (FIG. 6) correlate well to the orientation of the leads (FIG. 5).

The simple interelectrode impedance technique described above may be enhanced by making more accurate corrections using the appropriate field equations to calculate the monopolar and bipolar impedance of the electrodes. Also, other geometric methods may be employed using the improved "distance impedance" values to improve the mapping of the electrode orientations.

Next, the actual field measurement technique for determining relative electrode positions for multipolar leads of a neurostimulation system will be explained in connection with FIGS. 7-9. Such a technique utilizes field potential measurements of the implanted electrodes, and more particularly, field potential measurements on non-active electrodes caused by activation of other electrodes. In a preferred embodiment of this alternative embodiment, a constant current is sourced (anodes) and sunk (cathodes) from a predefined combination of electrodes. Such electrodes thus comprise the activated electrodes. Then, the resulting field potentials are measured at all other electrodes (those not involved in sourcing or sinking current), i.e., the non-activated electrodes. From these measured field potentials, the relative orientation of the electrodes, and the leads on which the electrodes are carried, may be determined. Advantageously, the use of field potentials represents an improvement over the use of impedance measurements, since the measured potential values are less subject to the confounding effects of the tissue impedance very close to the source/sink electrodes.

Figure 7:
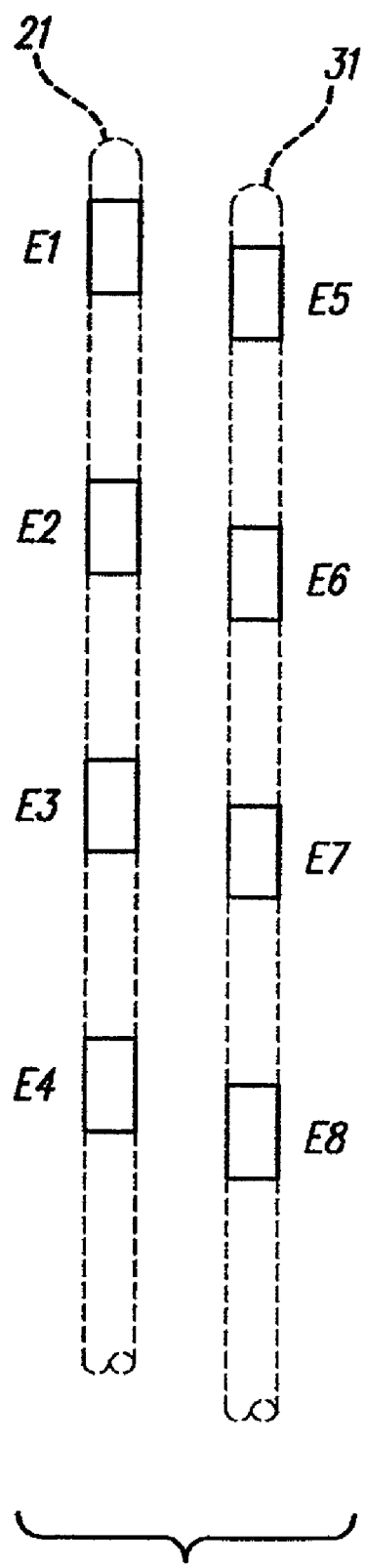
FIG. 7 depicts a representative fluoroscopic image of dual quadrapolar leads in a patient.
Figure 8:
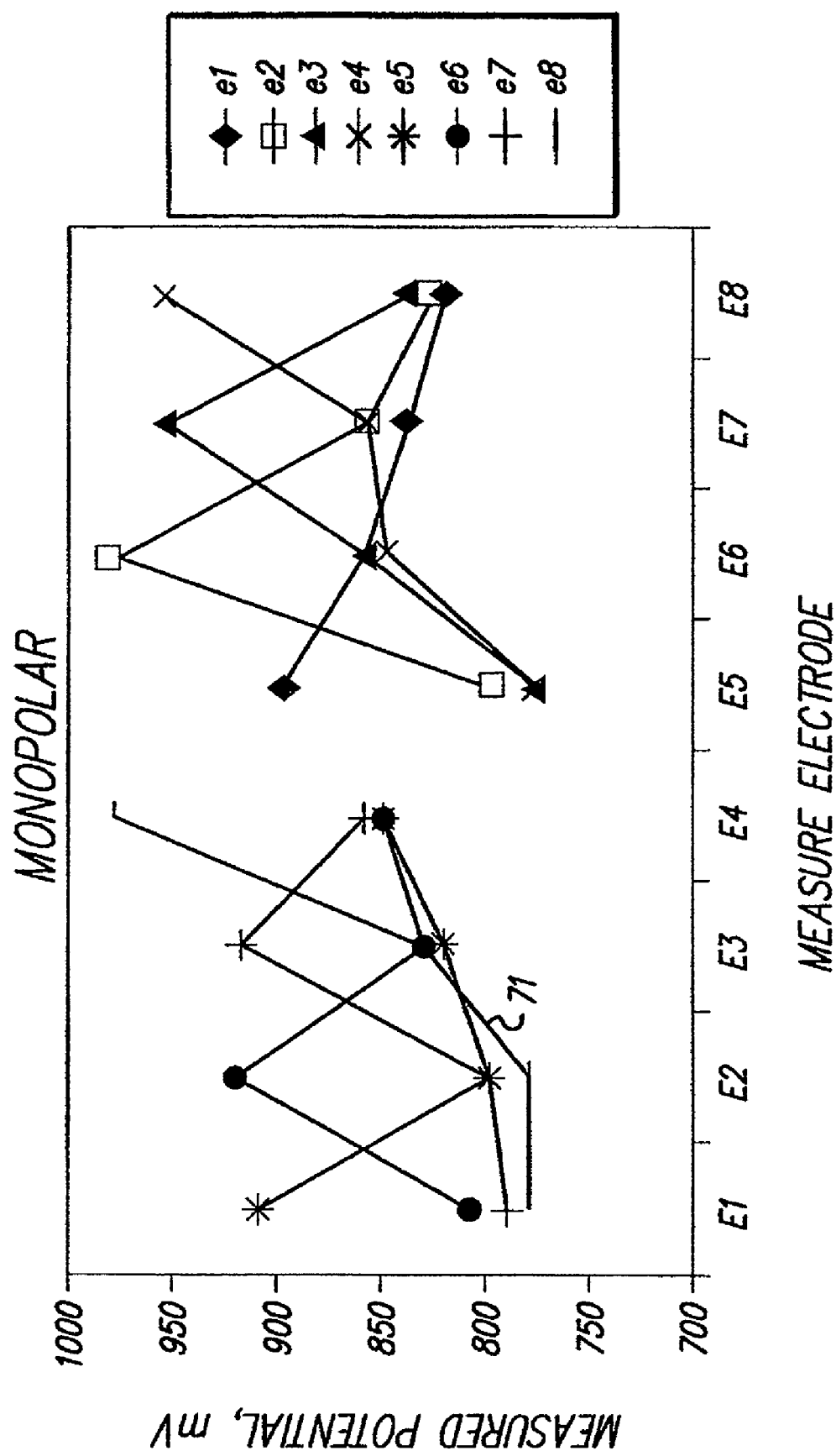
FIG. 8 illustrates, in accordance with another embodiment of the invention, the measured electrode potential of non-activated electrodes on the dual quadrapolar lead of FIG. 7 when the activated electrode is activated through monopolar stimulation.
Figure 9:
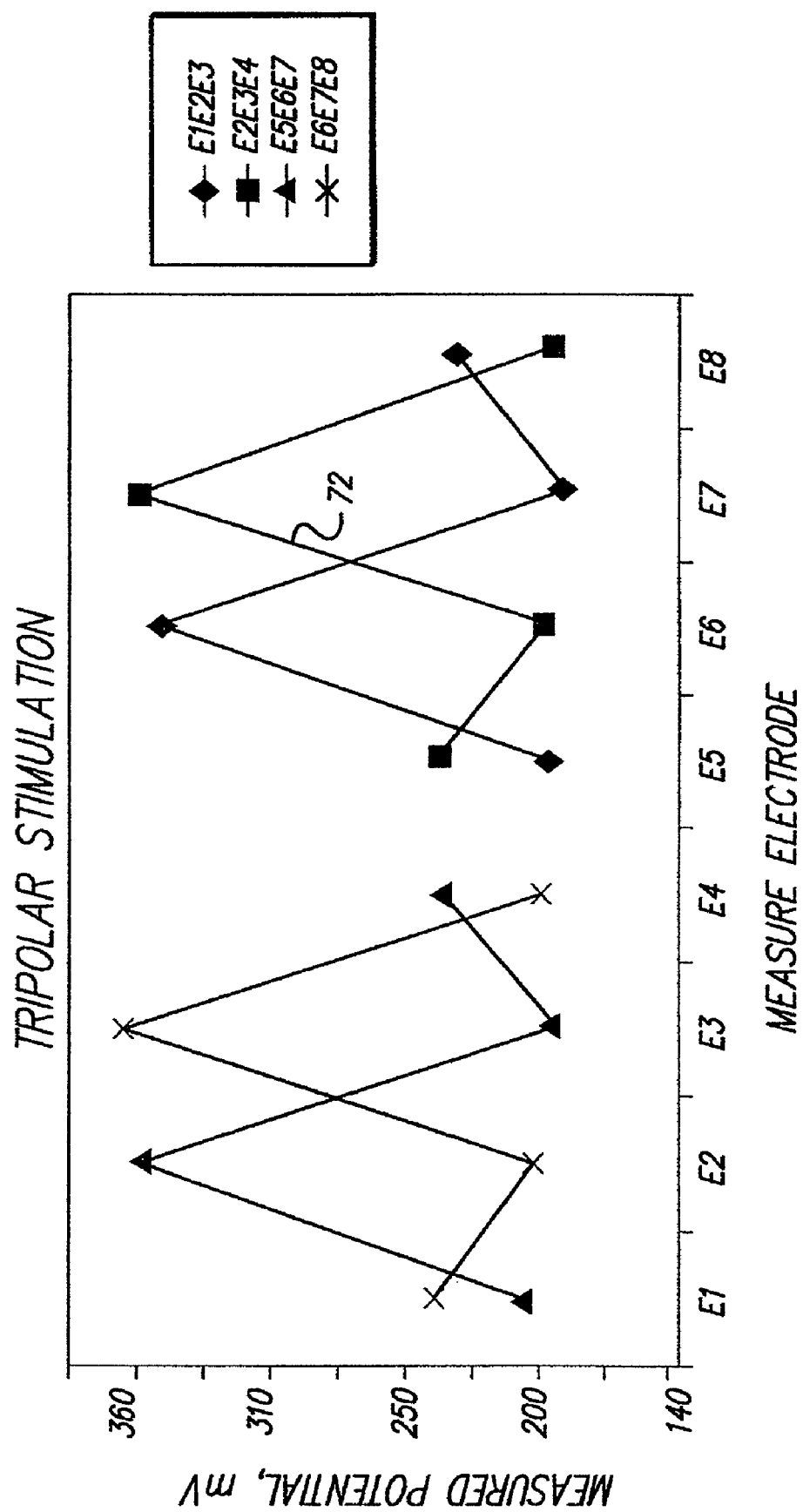
FIG. 9 illustrates the measured electrode potential of non-activated electrodes on the dual quadrapolar lead of FIG. 7 when the activated electrodes are activated through tripolar stimulation.

By way of example of this field potential measurement technique, consider FIGS. 7, 8 and 9. FIG. 7 represents the relative position of dual quadrapolar leads 21 and 31 after being implanted in a patient, as obtained using a fluoroscopic imaging device. In many instances, the necessary imaging equipment needed to obtain a fluoroscopic image, such as is shown in FIG. 7, is not readily available. Advantageously, the present field potential measurement technique represents an alternative approach to obtaining relative electrode position information rather than using an expensive and cumbersome imaging device.

Two combinations of anodes/cathodes are used to deliver current to the leads of the dual quadrapolar leads 21 and 31. The first technique is monopolar; that is, current delivered or sourced from one electrode (the cathode) and sunk to the return electrode $E_R$ (the anode). Thus, for each active monopolar combination, there are seven non-active electrodes on which the field potential may be measured. The second technique is flanked tripolar stimulation; that is, current delivered between two anodes and one cathode, with the cathode being flanked on each side by an anode.

In both the monopolar stimulation and the tripolar stimulation, a constant current is delivered to each electrode implanted in the patient's body while the field potential is measured on all other electrodes NOT involved in sinking/sourcing current. The constant current may be set to a sub-perception level, or to another suitable level that is comfortable for the patient.

The field potentials for the monopolar stimulation are plotted on the same chart in FIG. 8. The vertical axis is millivolts. As seen in FIG. 8, the electrodes closest to the source electrode have a high field potential (note: all plots in FIG. 8 and FIG. 9 are "negative", i.e., more negative potentials results in more positive measured values, as shown in the plots). Thus, for example, consider electrode E8 (curve 71), which has its highest field potential relative to electrode E4, and its lowest field potential relative to electrodes E1 and E2, and an intermediate potential relative to electrode E3. This corresponds to the actual electrode positions shown in FIG. 7, where electrode E8 is closest to electrode E4, somewhat further from electrode E3, and farthest from electrodes E2 and E1. A similar analysis for the monopolar stimulation fields of the other electrodes reveals a similar relationship: the electrodes closest to the source electrode have the higher potential.

The field potentials for the tripolar stimulation are plotted on the same chart in FIG. 9. Again, the vertical axis is millivolts. As seen in FIG. 9, a better relative orientation can be obtained than can be obtained with the monopolar stimulation. Those electrodes closest to the cathode have a high field potential while those electrodes closest to the anode have a lower field potential relative to the electrodes further away. For example, consider curve 72, which shows the field potential of the non-active electrodes relative to the tripolar stimulation of electrodes E2, E3, E4, with E2 and E4 being anodes, and E3 being a cathode. As seen in FIG. 9, curve 72 has a peak corresponding to electrode E7, which means electrode E7 is closest to the cathode E3. Curve 72 further has lows or valleys corresponding to electrodes E6 and E8, which means E6 and E8 are closest to anode electrodes E2 and E4. The actual orientation of the electrodes shown in FIG. 7 reveals that E6 is closest to E2, and E8 is closest to E4. Thus, it is seen that those electrodes closest to the flanked cathodic electrode have a high field potential while those electrodes closest to the anodic electrodes, on either side of the cathodic electrode, have a lower field potential relative to the electrodes further away.

Hence, it is seen that by measuring the field potential of the non-active electrodes, when active electrodes are stimulated at constant current levels, e.g., subperception levels, the relative orientation of the neurostimulation leads may be determined. Once known, the relative orientation may be used to perform any one or more of a variety of corrective actions, as will be described in further detail below.

Next, the estimated field potential technique for determining relative electrode positions for multipolar leads of a neurostimulation system will be explained in connection with FIGS. 10 and 11. Like the previous technique, this technique analyzes the field potentials at the implanted electrodes. Unlike the previous technique, however, this technique estimates the field potentials at the implanted electrodes based on measured electrical parameters, and in particular, measured monopolar and bipolar impedances. Notably, this technique has the advantage of minimizing the number of actual measurements performed by the neurostimulation system in the case where impedance measurements must already be taken to effect another function, such as verifying contact continuity, remaining battery charge estimation, detecting electrode shorts, etc. That is, in the previous technique, actual field potential measurements would have to be measured to determine the relative orientation of the electrodes E1-E16 (shown in FIG. 1) in addition to the impedance measurements measured to effect a function unrelated to the relative electrode orientation determination.

Figure 10:
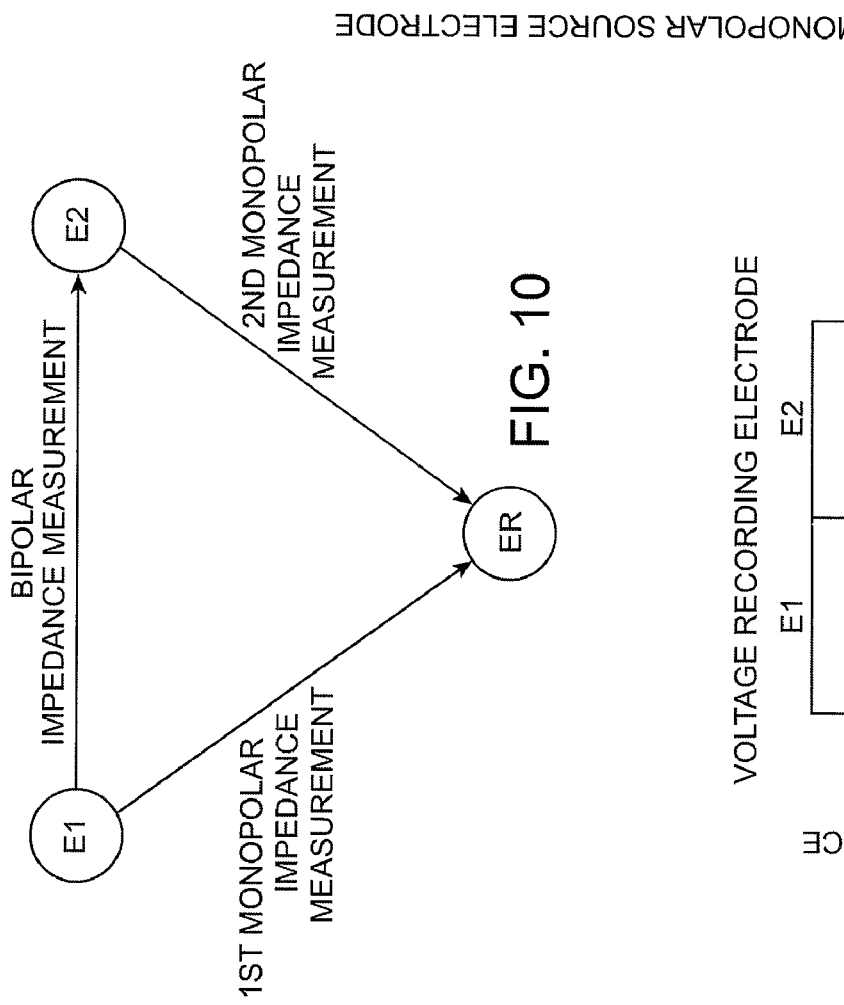
FIG. 10 illustrates an arrangement of two electrodes and a return electrode, wherein monopolar impedance measurements are taken between the two electrodes and the return electrodes, and a bipolar impedance measurement is taken between the two electrodes.

As illustrated in FIG. 10, a first monopolar impedance measurement is taken between a first one of the electrodes E1-E16 (in this case electrode E1) and the return electrode $E_R$, a second monopolar impedance measurement is taken between a second one of the electrodes E1-E16 (in this case, electrode E2) and the return electrode $E_R$, and a bipolar impedance measurement is taken between the first and second ones of the electrodes E1-E16 (in this case, between electrodes E1 and E2). As will be described in further detail below, the field potential that would have been created at electrode E2 had electrode E1 been activated in a monopolar manner can then be estimated based on these impedance measurements. The impedance measurements can be taken in the same manner described above with respect to the first technique. Notably, the estimate of the field potential at electrode E2 will be approximately equal to the actual field potential measured at electrode E2, as an inactive electrode, assuming that electrode E1 would have been activated. The monopolar and bipolar impedance measurements can be performed on each pair of electrodes E1-E16 to obtain field potential estimations for each electrode (i.e., 15 field potential estimations for each electrode corresponding to 15 assumed activations of the remaining electrodes).

Figure 11:
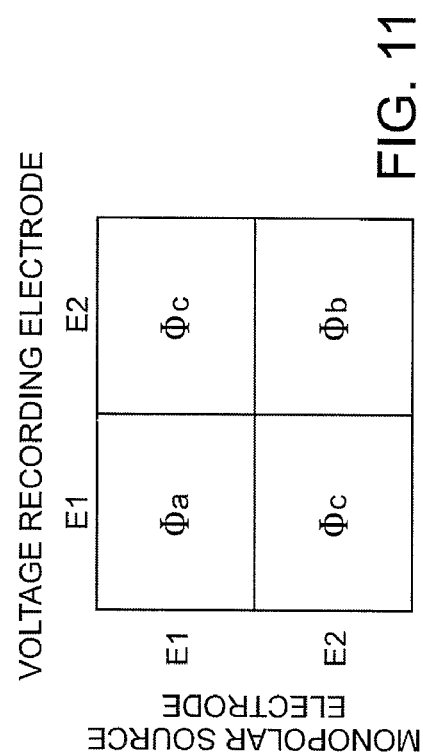
FIG. 11 is a field potential matrix created when the two electrodes of FIG. 10 are sourcing current while field potentials are measured on the two electrodes.

Referring now to FIG. 11, the theory behind estimating field potentials based on monopolar and bipolar impedance measurements will now be explained. If electrode E1 sources current in a monopolar fashion to electrode $E_R$, a field potential $\Phi_a$ is created at electrode E1. Similarly, if electrode E2 sources current in a monopolar fashion to electrode $E_R$, a field potential $\Phi_b$ is created at electrode E2. By reciprocity, a field potential $\Phi_c$ is seen on electrode E1 when electrode E2 sources current, and on electrode E2 when electrode E1 sources current. Assuming that the field potentials $\Phi_a$-$\Phi_c$, are unknown, linear superposition can be applied to estimate field potentials on electrodes E1, E2 when both are used to source/sink current simultaneously. Note that the field potential $\Phi_a$ is equal to the monopolar impedance of electrode E1 if the source current is unit value, and the field potential $\Phi_b$ is equal to the monopolar impedance of electrode E2 if the source current is unit value. Solving for bipolar impedance/field potentials, and letting electrode E1 source unit current and electrode E2 sink unit current, the bipolar field potential at electrode E1 will equal the monopolar field potential $\Phi_a$—the monopolar field potential $\Phi_c$, and the bipolar field potential at electrode E2 will equal the monopolar field potential $\Phi_c$—the monopolar field potential $\Phi_b$. Assuming that the bipolar impedance $R_{bp}$ between electrodes E1 and E2 equals the voltage potential ($\Delta V$) between electrodes E1 and E2 divided by the unit current (I) between electrodes E1 and E2, then $R_{bp}=((\Phi_a-\Phi_c)-((\Phi_c-\Phi_b))/1=\Phi_a+\Phi_b-2\Phi_c$. Because the monopolar field potentials $\Phi_a$ and $\Phi_b$ at electrodes E1 and E2 respectively equal the monopolar impedances $R_{mp1}$ and $R_{mp2}$ at electrodes E1 and E2, assuming unit current, it follows that $\Phi_c=-(R_{bp}-R_{mp}-R_{mp2})/2$. Thus, the field potential at any electrode due to active passage of current at other electrode(s) can be estimated based on measured monopolar/bipolar impedances by solving for the electrical voltage potential $\Phi_c$.

Notably, while this equation has been presented herein to estimate a field potential $\Phi_c$ for the purpose of determining the migration of electrical leads or electrodes, any one of the monopolar impedances between two electrodes and a return electrode, the bipolar impedance between the two electrodes, and the field potential at one of the two electrodes can be estimated by actually measuring the remaining two of the monopolar impedances, bipolar impedance, and field potential to solve the equation for the estimated parameter. Thus, instead of measuring all three of these parameters, only two of them need to be actually measured, while the remaining parameter can be estimated.

While estimation of field potentials from monopolar and multipolar impedance measurements (or estimation of a multipolar impedance using field potentials and monopolar impedance; or estimation of a monopolar impedance using field potentials and multipolar impedance) has been illustrated with a simple two-contact (plus distant return for monopolar measurements) system, it is noted that many monopolar and multipolar combinations with two or more electrodes could be used to estimate field potentials (or impedances) given the linearity and reciprocity associated with the solution method.

Figure 12:
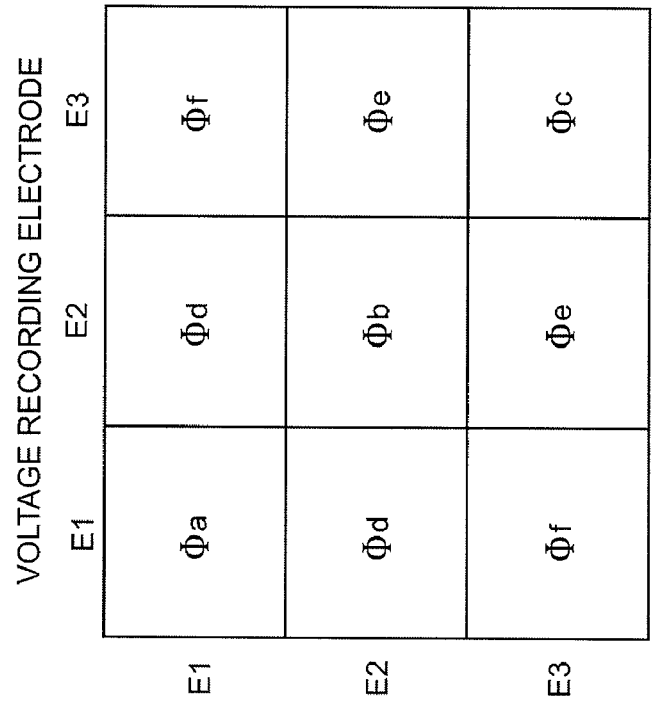
FIG. 12 is a field potential matrix created when the three electrodes are sourcing current while field potentials are measured on the three electrodes.

For example, referring now to FIG. 12, if electrode E1 sources current in a monopolar fashion to electrode $E_R$, a field potential $\Phi_a$ is created at electrode E1; if electrode E2 sources current in a monopolar fashion to electrode $E_R$, a field potential $\Phi_b$ is created at electrode E2; and if electrode E3 sources current in a monopolar fashion to electrode $E_R$, a field potential $\Phi_c$ is created at electrode E3. By reciprocity, a field potential $\Phi_d$ is seen on electrode E1 when electrode E2 sources current, and on electrode E2 when electrode E1 sources current; a field potential $\Phi_e$ is seen on electrode E2 when electrode E3 sources current, and on electrode E3 when electrode E2 sources current; and a field potential $\Phi_f$ is seen on electrode E1 when electrode E3 sources current, and on electrode E3 when electrode E1 sources current.

Assuming that field potentials $\Phi_a$-$\Phi_f$ are initially unknown, there may be a variety of ways to estimate the field potentials $\Phi_a$-$\Phi_f$ using linear supposition. For example, the field potentials $\Phi_a$-$\Phi_f$ can be estimated by configuring the electrodes E1-E3 in three configuration (1 tripolar configuration, 1 bipolar configuration, and 1 monopolar configuration).

Assume for the tripolar configuration that unit values of +0.5, −1.0, and +0.5 are respectively applied to electrodes E1-E3, then the respective monopolar field potentials m1-m3 on electrodes E1-E3 will be will m1 $=0.5\Phi_a+0.5\Phi_f-\Phi_d$; m2$=-\Phi_b+0.5\Phi_e+0.5\Phi_d$; and m3$=0.5\Phi_c+0.5\Phi_f-\Phi_e$. Assume for the bipolar configuration that unit values of +1.0 and −1.0 are respectively applied to electrodes E1 and E2, then the respective monopolar field potentials m4 and m5 on electrodes E1 and E2 will be will m4$=\Phi_a-\Phi_d$; and m5$=\Phi_d-\Phi_b$. Assume for the monopolar configuration that a unit value of −1.0 is applied to electrode E3, then a monopolar field potential m6 on electrode E3 will be −$\Phi_c$.

Based on the field potential measurements m1-m6, the six unknown field potentials $\Phi_a$-$\Phi_f$ can be solved using common algebraic techniques or linear algebraic techniques, as follows:

$\Phi_a=2m1-4m2-2m3+4m5-m6$ $\Phi_b=2m1-4m2-2m3-m4+3m5-m6$ $\Phi_c=-m6$ $\Phi_d=2m1-4m2-2m3-m4+4m5-m6$ $\Phi_e=2m1-2m2-2m3-m4+2m5-m6$ $\Phi_f=4m1-4m2-2m3-2m4+4m5-m6$

The calculated field potentials $\Phi_a$-$\Phi_f$ can be used to estimate bipolar impedances and monopolar impedances and potential differences for arbitrary electrode configurations. That is, assuming a unit current, the monopolar impedances on electrodes E1-E3 will be the field potentials $\Phi_a$-$\Phi_c$, and the bipolar impedances on electrodes E1, E2 will be $\Phi_a$-$\Phi_b$-$2\Phi_d$, bipolar impedances on electrodes E2, E3 will be $\Phi_b$-$\Phi_c$-$2\Phi_e$, and bipolar impedances on electrodes E1, E3 will be $\Phi_a$-$\Phi_c$-$2\Phi_f$.

Figure 13A:
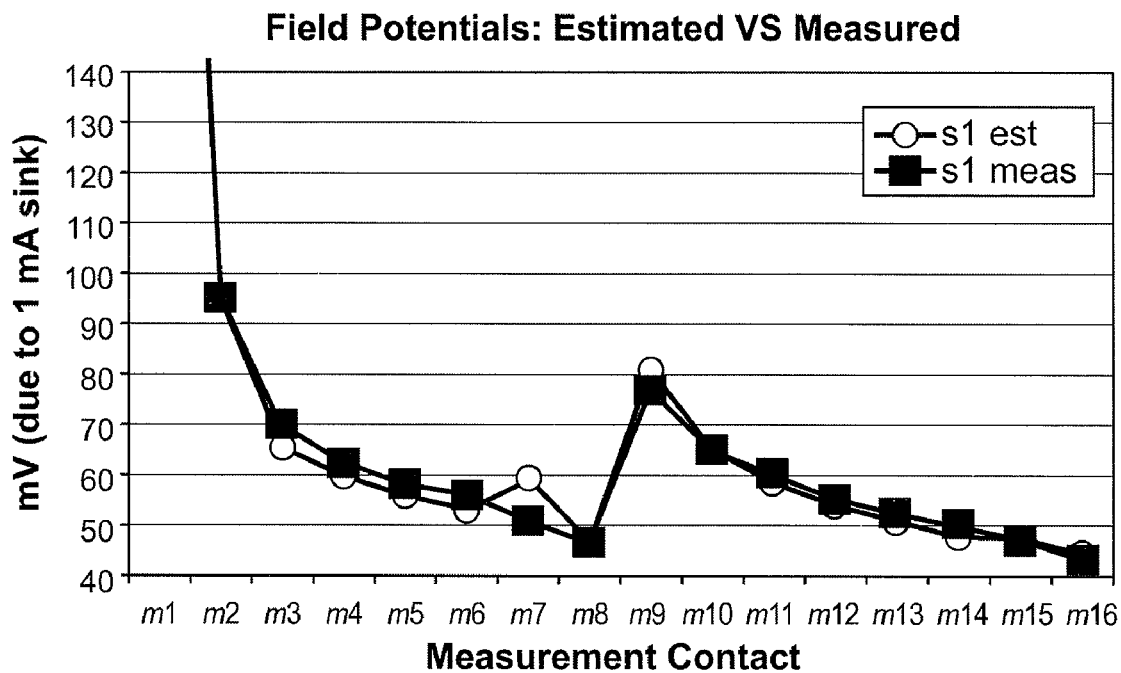
FIG. 13 illustrates a comparison between the actual measured field potential on leads of FIG. 1 and the estimated field potential on the leads of FIG. 1.
Figure 13B:
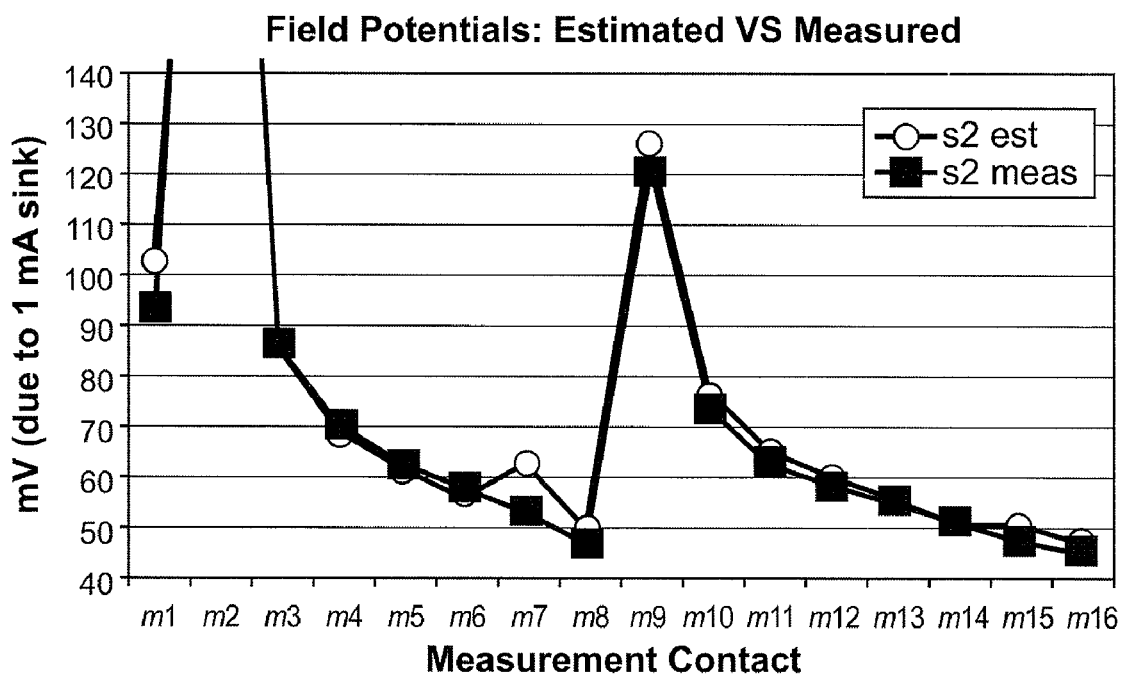
Figure 13C:
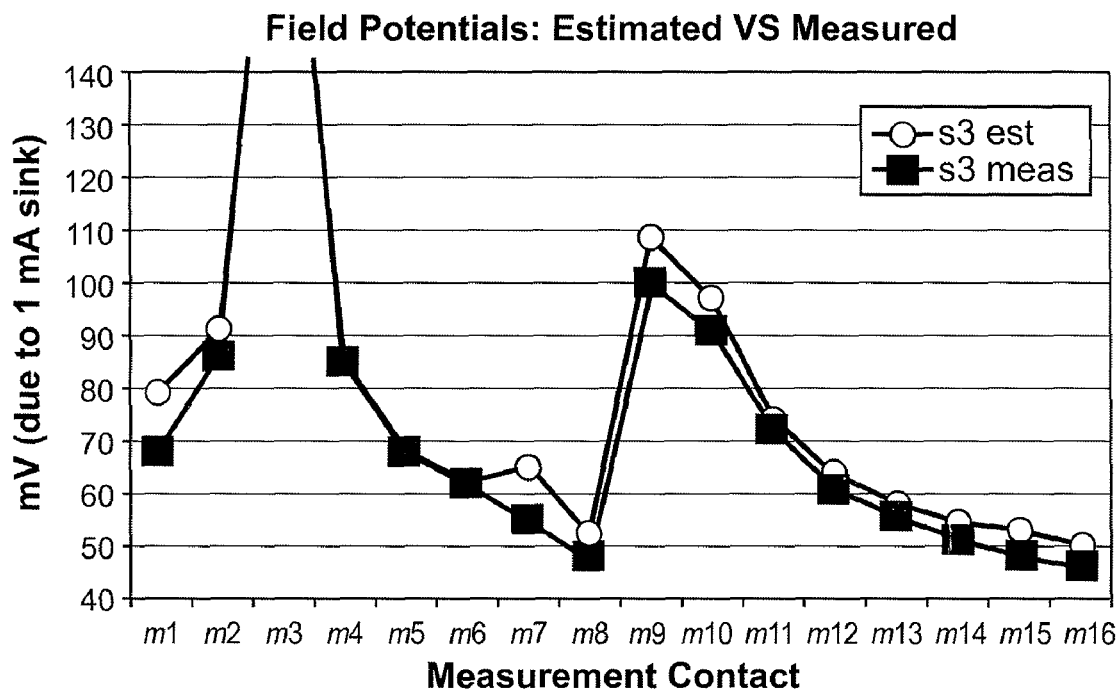
Figure 13D:
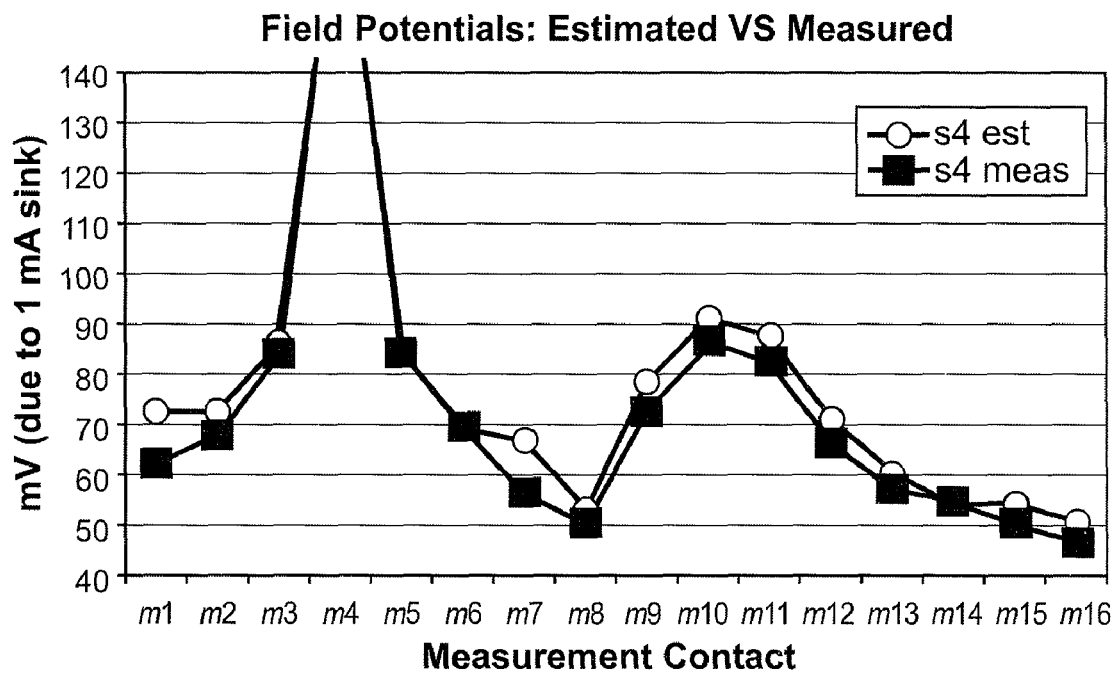
Figure 13E:
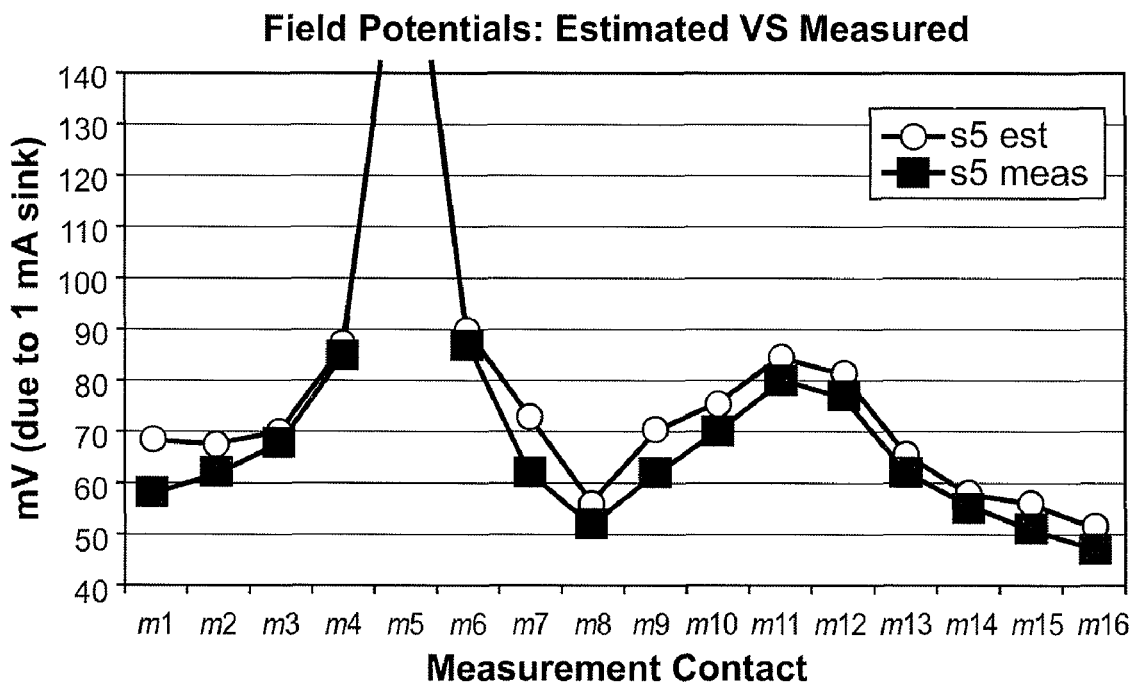
Figure 13F:
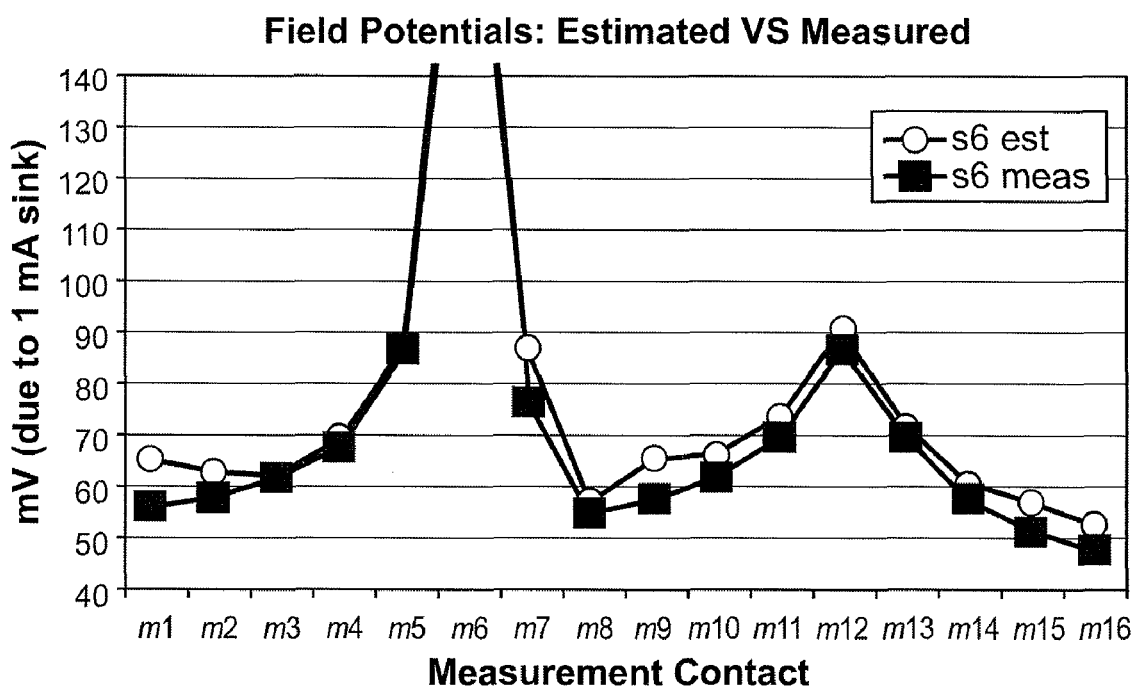
Figure 13G:
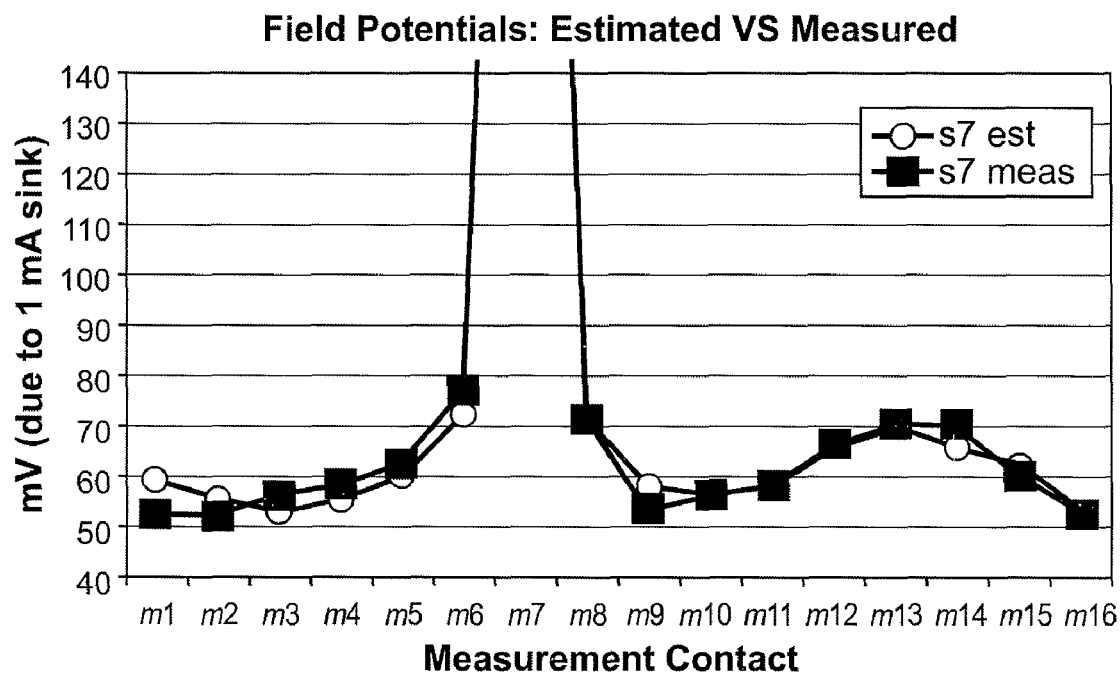
Figure 13H:
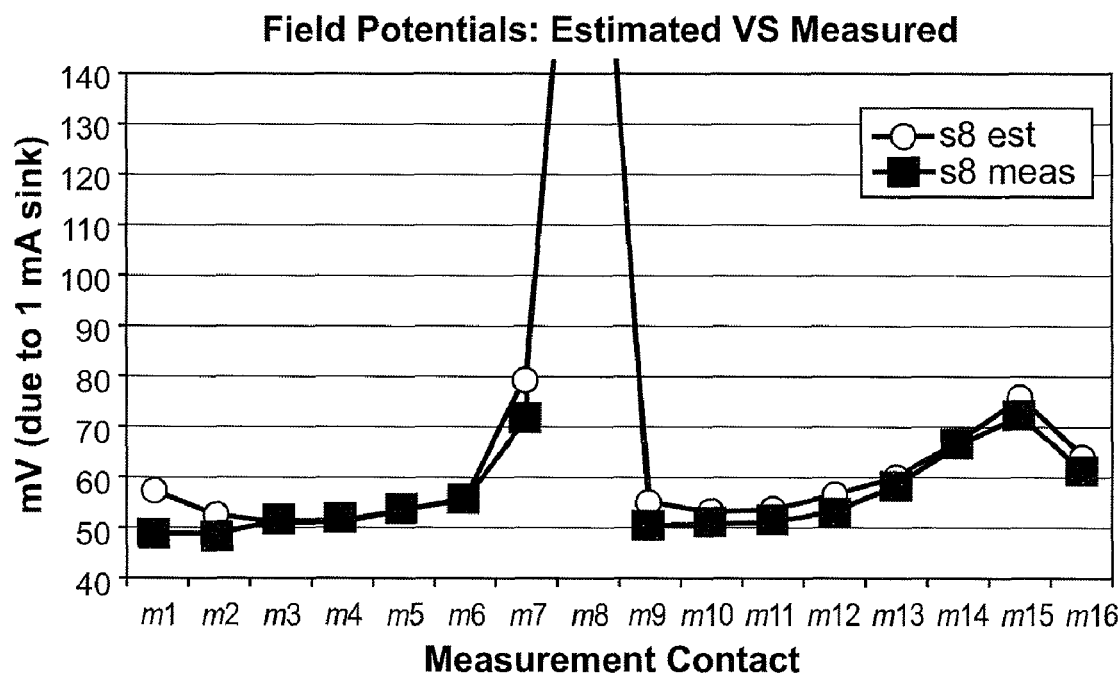
Figure 13I:
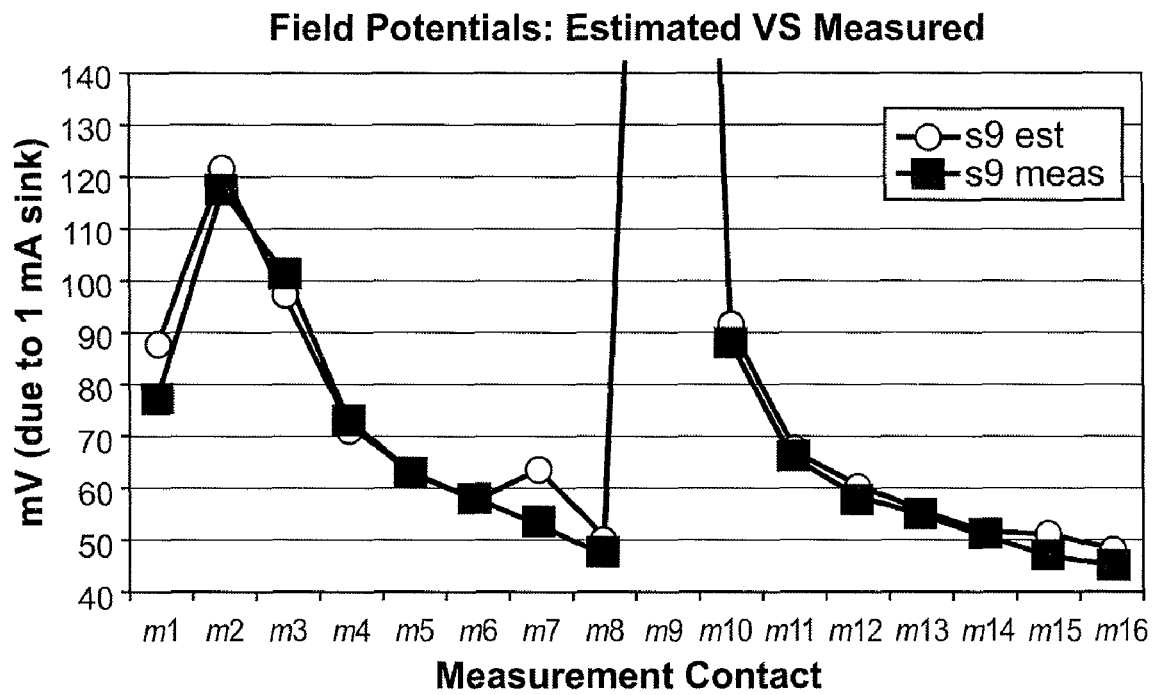
Figure 13J:
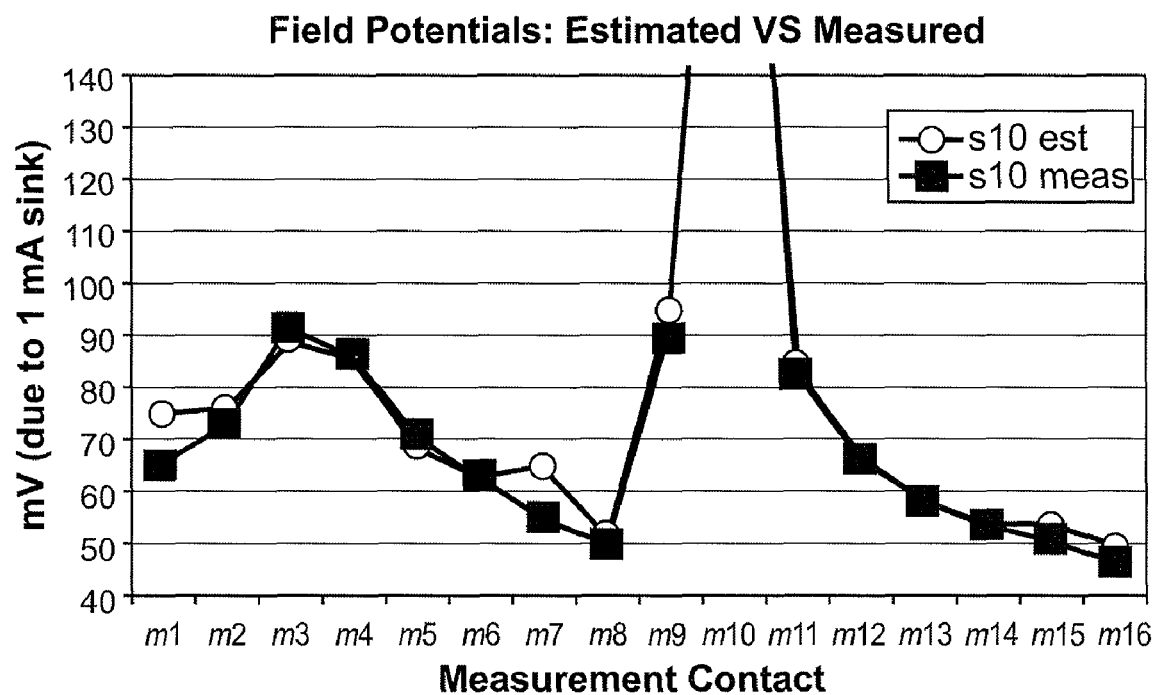
Figure 13K:
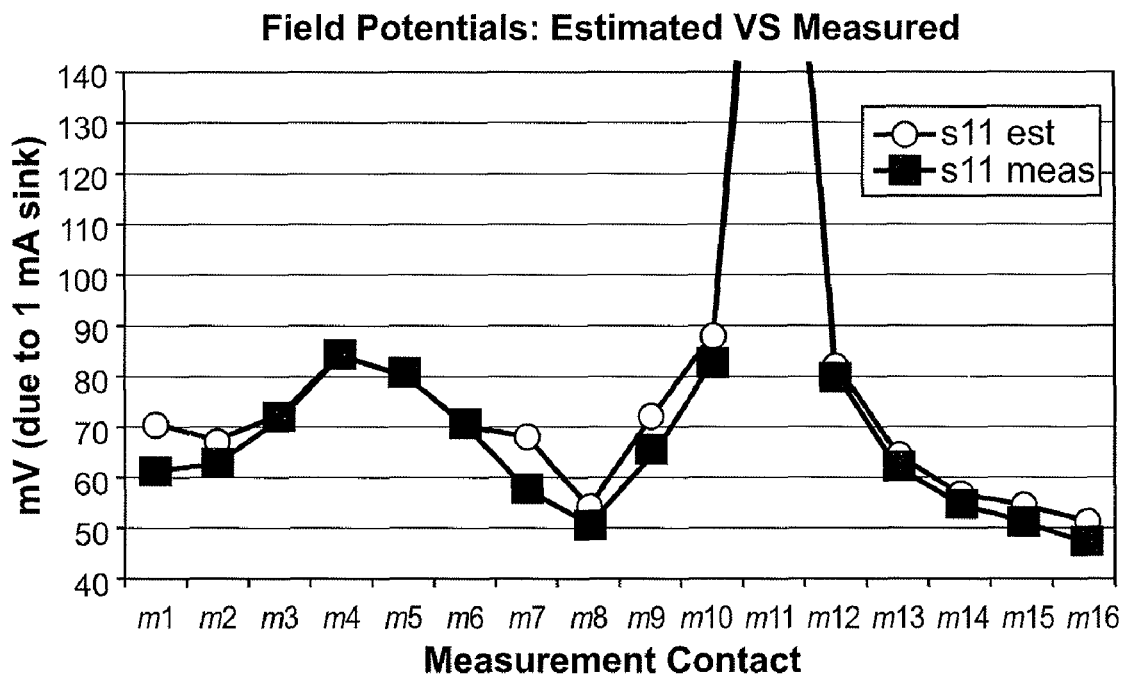
Figure 13L:
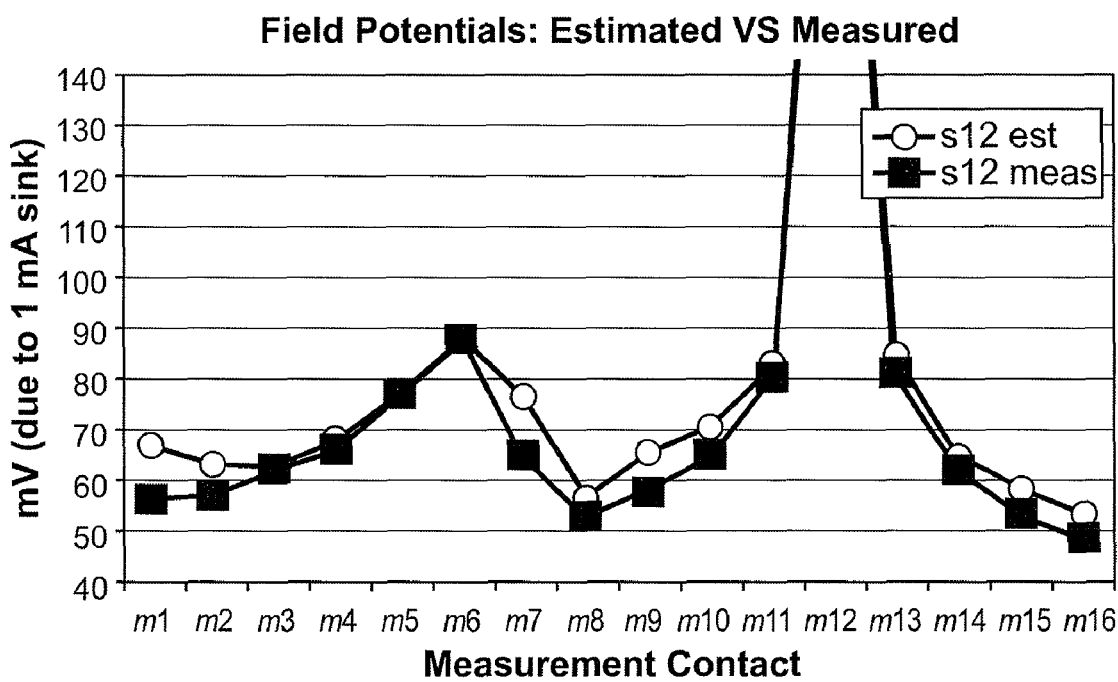
Figure 13M:
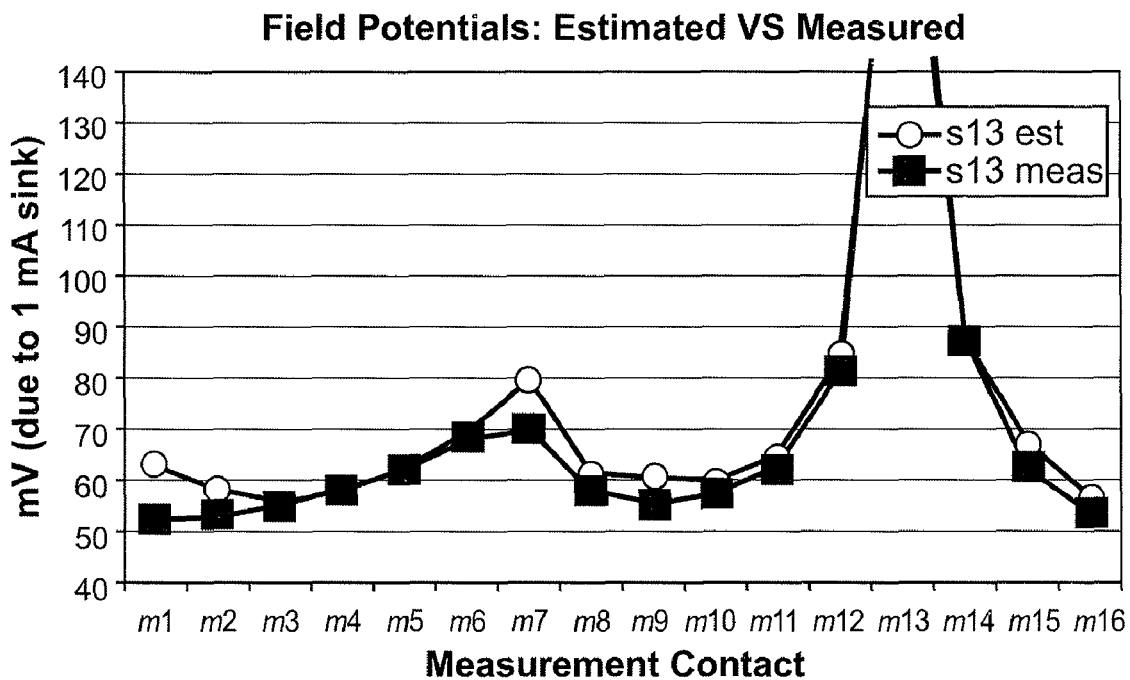
Figure 13N:
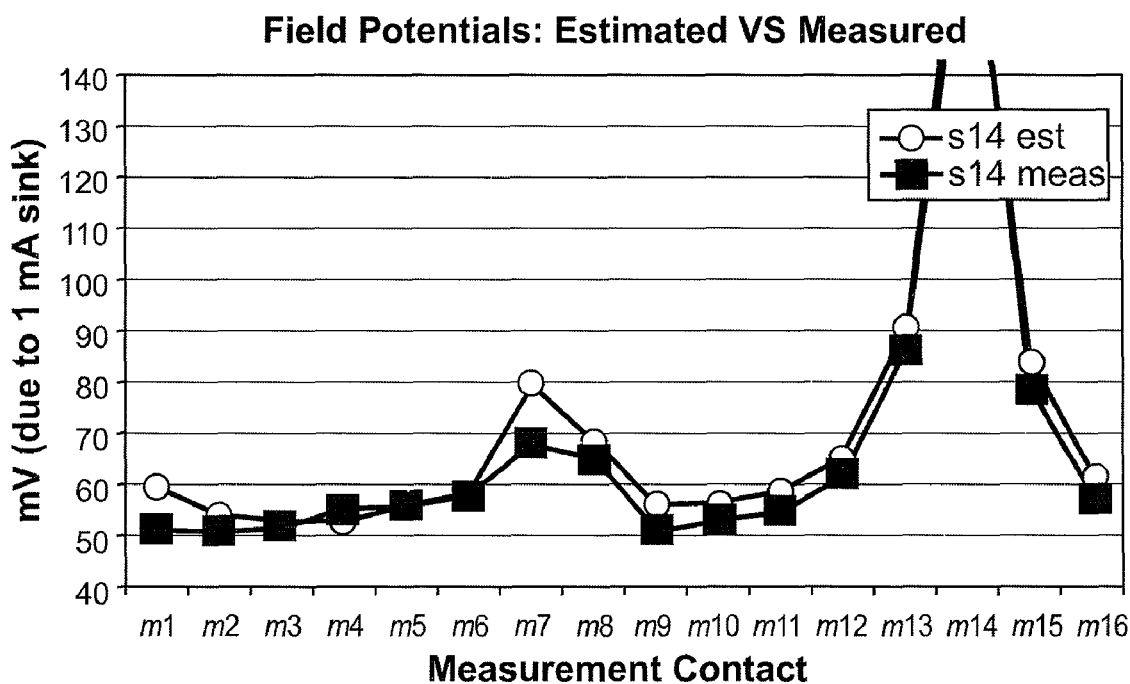
Figure 13O:
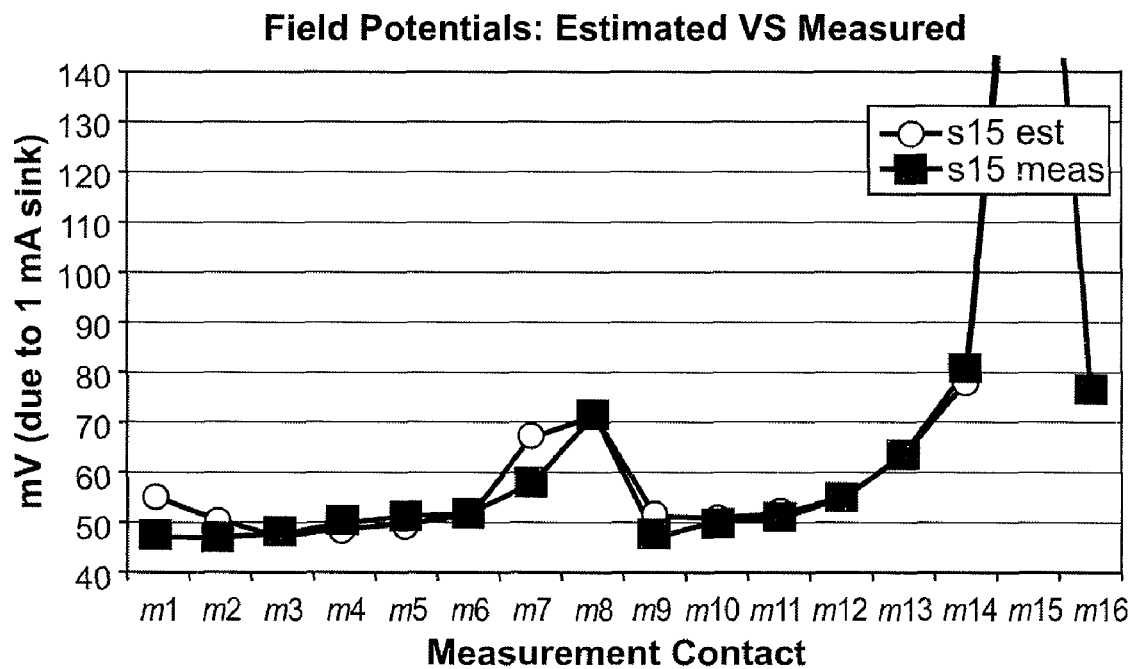
Figure 13P:
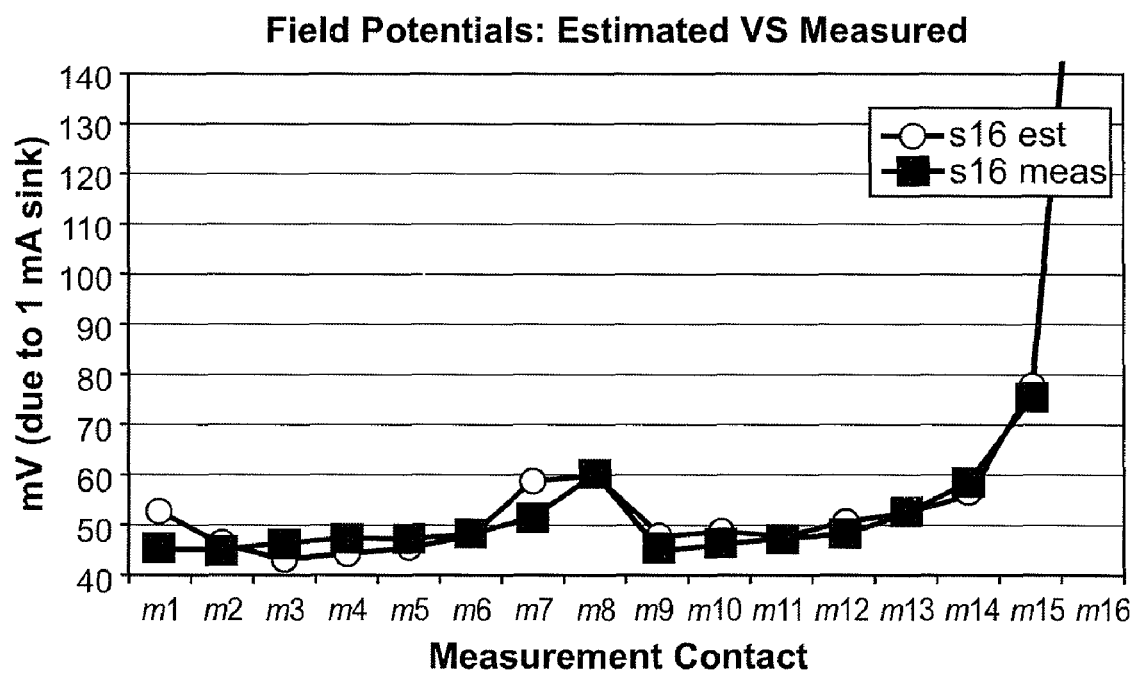

Referring to FIGS. 13A-13P, it can be seen that the estimated field potential of any electrode calculated in accordance with this equation is approximately the same as the field potential actually measured at the electrode in response to the monopolar delivery of electrical current from another electrode to the return electrode. In particular, two percutaneous leads carrying eight electrodes (similar to the leads 20, 30 shown in FIG. 1) each were introduced into a sausage loaf, which has been found to closely simulate the introduction leads into the spinal column of a patient. In each of the cases, current was sourced from a different electrode in a monopolar manner and actual field potentials were measured on each of the other electrodes. In each of the cases, a monopolar impedance was also measured at a different electrode, bipolar impedances were measured between the different electrode and the other electrodes, and field potentials were estimated for the other electrodes.

For each case, the actual and estimated field potentials were then plotted together, as shown in FIGS. 13A-13P. The vertical axis represents millivolts (in response to a 1 mA current sink), and the horizontal axis represents the electrode designation (m1-m16). The electrode having the highest field potential will be the closest electrode to the electrode that is currently sourcing the current (in the case where actual field potentials are measured) or the closest electrode to the electrode at which the monopolar and bipolar impedances are measured (in the case where the field potentials are estimated. More significant to the determination of the relative positions of the leads carrying the electrodes, the electrode having the highest field potential on one lead will typically be the closest electrode to the electrode that is sinking the monopolar current from the other lead or the closest electrode to the electrode at which the monopolar and bipolar impedances are measured. For example, referring to FIG. 13A, electrode E9 has the highest potential of the electrodes on the second lead relative to the electrode E1 on the first lead, and thus, is closest in proximity to the electrode E1.

Figure 14:
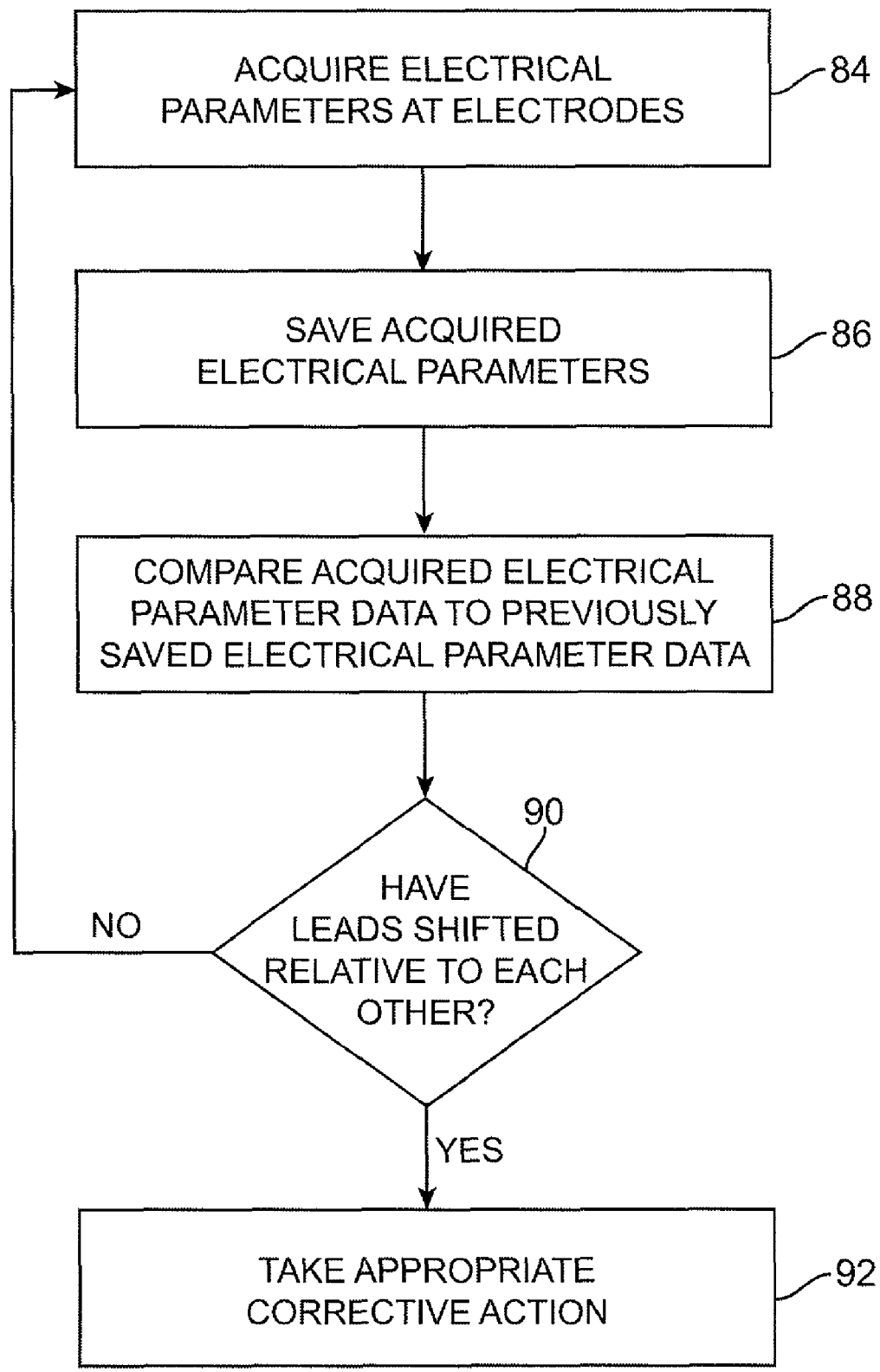
FIG. 14 is a flowchart that highlights the main steps used with one embodiment of the present invention.

Next, with reference to FIG. 14, a flowchart is shown that illustrates the main steps that may be used to carry out and apply the techniques described above. First, the amplitudes of the pertinent electrical parameters are acquired at the electrodes (block 82). For example, if the interelectrode impedance measurement technique is used, the pertinent electrical parameters will be impedance vectors, as described above with respect to FIGS. 4-7. If the field potential measurement technique is used, the pertinent electrical parameters will be actual field potentials, as described above with respect to FIGS. 8-9. In this case, suitable stimuli, e.g., subperception stimuli, are applied to different electrodes as activated electrodes. While the stimulus is being applied to each of the activated electrodes, field potentials at the non-activated electrodes are measured. If the field potential estimation technique is used, the electrical parameter will be an estimated field potential, as described above with respect to FIG. 10-12. In this case, the monopolar impedances between the electrodes and the return electrode are measured, the bipolar impedances between the electrodes are measured, and the field potentials at the electrodes are estimated therefrom.

The amplitudes of the acquired electrical parameters are then saved (block 86), and the stored electrical parameter data is compared to previously-saved electrical parameter data for the same electrodes (block 88). The previously-saved electrical parameter data may have been obtained during initial implantation of the leads, or during the last visit (several weeks or months ago) to the doctor. Or, the previously-saved electrical parameter data may have been obtained just a new hours or minutes ago at a time when the patient's body had assumed a different posture position. Regardless of when the previously-saved electrical parameter data was obtained, the purpose of the comparison performed at block 88 is to determine if the relative position of the leads has changed, which change in position would also have caused a relative change in the position of the electrodes carried on the leads. Such determination may be made by analyzing the electrical parameter data (block 90) as described above in connection with FIGS. 4-7 (where the electrical parameter data are impedance vectors), in connection with FIGS. 8-9 (where the electrical parameter data are actual field potentials), or in connection with FIGS. 10-12 (where the electrical parameter data are estimated field potentials), to determine whether the relative electrode orientation has changed.

The magnitude of the difference in the compared electrical parameter data may advantageously provide a relative measure of how far the lead has shifted or moved since the last electrical parameter data was obtained. If a determination has been made that the leads (electrodes) have not shifted relative to each other (block 90), the process returns to block 84. Advantageously, if a determination has been made that the leads (electrodes) have shifted relative to each other (block 90), appropriate correction action may be taken, as needed (block 92). The corrective action taken at block 92 may include, for example, simply tracking the lead migration over time, so that other corrective action, e.g., surgery to reposition the leads, can be taken when necessary. Even if new surgery to reposition the leads is not needed, simply mapping the lead migration overtime will enable reprogramming of the stimuli parameters as needed so that a desired effect can be obtained regardless of the lead movement.

The corrective action may further include setting up stimulation configurations and parameters for providing nominal stimulation suitable for the electrodes in their new relative positions. For example, the amplitude of the stimulus applied to one electrode may be decreased if it is determined that the electrode has migrated closer to another stimulating electrode of the same polarity during stimulation, thereby preserving approximately the same stimulation effect for the patient. Alternatively, the amplitude of the stimulus applied to the electrode may be increased if the electrode has migrated closer to a stimulating electrode of the opposite polarity. Such amplitude adjustments may be made manually or automatically, depending on the mode of operation of the neurostimulation system.

Yet another corrective action that may be taken at block 92 is to adjust the distribution of the stimuli to a new location through navigation. Navigation, as described in the previously referenced patent documents, involves electronically shifting the stimulus current from one group of electrodes to another so as to shift or move the location where the patient feels the most beneficial paresthesia, and/or receives the most benefit. Such navigation allows the neurostimulation system to be quickly "fitted" to a given patient. Fitting the neurostimulation system to the patient is necessary after the system is first implanted, and may also be necessary whenever the leads (electrodes) have moved. The neurostimulation system provides a relatively easy way to determine whether such lead movement has occurred, and thereby whether a refitting is or may be necessary.

Yet additional corrective action that may be taken at block 92 in response to a determination that lead migration or postural changes have occurred includes manually or automatically adjusting the stimulation energy to a previously-defined optimal field potential.

It is thus seen that the present invention uses a measure or estimation of impedance or electric field to determine relative lead positions for multipolar leads in a multi-lead configuration of a neurostimulation system, e.g., a spinal cord stimulation system. It is also seen that the neurostimulation system uses impedance or electric field measurements or estimations to determine relative lead positions, which impedance or electric field measurement estimations may be used as an automated or assistive method for setting up a programmer for navigation, other programming, or diagnostic evaluations in spinal cord (or other neural) stimulation. It is additionally seen that the neurostimulation system may be directed to the storing of impedance or electric field maps to chronically track relative lead positions in a programmer linked to a database, along with other patient data.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of performing a medical procedure using a plurality of electrodes implanted within a patient, comprising:
   measuring a first monopolar electrical impedance between a first one of the electrodes and a return or reference electrode;
   measuring a second monopolar electrical impedance between each of at least one of the electrodes and the return or reference electrode;
   measuring a bipolar electrical impedance between the first one of the electrodes and each of the at least one electrode;
   determining the amplitude of a field potential at each of at least one of the electrodes based on the measured first monopolar electrical impedance, each of the second monopolar electrical impedances, and each of the measured bipolar electrical impedances; and
   determining the relative positions of the electrodes based on each of the determined field potential amplitudes.

2. The method of claim 1, wherein the electrodes are carried by a plurality of leads, the method further comprising determining the relative positions of the leads based on the determined field potential amplitude of the each of the at least one electrode.

3. The method of claim 2, wherein the entireties of the leads are implanted within the tissue of the patient.

4. The method of claim 1, further comprising:
   determining if a change in each of the determined field potential amplitudes has occurred; and
   analyzing the change in each of the determined field potential amplitudes to determine whether a change in the relative position of the electrodes has occurred.

5. The method of claim 4, further including initiating corrective action when a determination is made that the relative position of the electrodes has changed.

6. The method of claim 5, wherein the corrective action is initiated automatically.

7. The method of claim 5, wherein the corrective action includes adjusting the amplitude of tissue stimulating electrical energy applied to selected ones of the electrodes.

8. The method of claim 5, wherein the corrective action includes changing selected ones of the electrodes through which tissue stimulating electrical energy is applied.

9. The method of claim 5, wherein the corrective action includes performing a surgical revision on the patient to physically readjust the electrodes.

10. The method of claim 1, wherein the electrodes are carried by a plurality of leads, and wherein the change in each of the determined field amplitudes are analyzed to determine migration of the leads relative to each other.

11. The method of claim 10, wherein the entireties of the leads are implanted within the tissue of the patient.

12. The method of claim 1, further comprising displaying the determined relative positions of the electrodes.

13. The method of claim 1, wherein the at least one electrode comprises a plurality of the electrodes.

14. The method of claim 1, where the field potential amplitude determination comprises directly measuring the field potential amplitude directly at each of the at least one electrode.

15. The method of claim 1, wherein the amplitude of the field potential at each of the at least one electrode is estimated in accordance with the equation $\Phi=(I_{bp}-I_{mp1}-I_{mp2})/2$, where $\Phi$ equals the amplitude of the field potential, $I_{bp}$ equals the respective bipolar electrical impedance, $I_{mp1}$ equals the first monopolar electrical impedance, and $I_{mp2}$ equals the respective second monopolar electrical impedance.

16. The method of claim 1, further comprising storing each of the determined field potential amplitudes.

17. The method of claim 1, further applying conveying tissue stimulating electrical energy to selected ones of the electrodes, thereby providing therapy to the patient.

18. A method for performing a medical procedure using a plurality of electrodes implanted within a patient, comprising:
    measuring a first monopolar impedance between a first one of the electrodes and a return or reference electrode;
    measuring a second monopolar impedance between a second one of the electrodes and the return or reference electrode;
    measuring a bipolar impedance between the first electrode and the second electrode; and
    estimating an amplitude of a field potential at the second electrode based on the first and second monopolar impedances and the bipolar impedance.

19. The method of claim 18, wherein the estimated field potential amplitude is approximately equal to the actual field potential at the second electrode when an electrical stimulus is conveyed between the first electrode and the return or reference electrode.

20. The method of claim 18, further comprising determining whether a change in the relative positions of the electrodes has occurred based on the estimated field potential amplitude.

21. The method of claim 20, further comprising performing a function unrelated to the determining whether a change in the relative positions of the electrodes has occurred based on at least one of the first monopolar impedance, second monopolar impedance, and bipolar impedance.

22. The method of claim 21, wherein the function is one or more of determining a remaining battery life of neurostimulator and detecting an electrical short within the neurostimulator.

23. The method of claim 20, further including initiating corrective action when a determination is made that the relative position of the electrodes has changed.

24. The method of claim 20, wherein the corrective action is initiated automatically.

25. The method of claim 20, further comprising displaying the determined relative positions of the electrodes.

26. The method of claim 21, wherein the amplitude of the field potential is estimated in accordance with the equation $\Phi=(I_{bp}-I_{mp1}-I_{mp2})/2$, where $\Phi$ equals the magnitude of the field potential, $I_{bp}$ equals the bipolar electrical impedance, $I_{mp1}$ equals the first monopolar electrical impedance, and $I_{mp2}$ equals the second monopolar electrical impedance.

27. A method for performing a medical procedure using a plurality of electrodes implanted within a patient, comprising:
    performing two of the following: (1) measuring a first monopolar impedance between a first one of the electrodes and a return or reference electrode, and measuring a second monopolar impedance between a second one of the electrodes and the return or reference electrode; (2) measuring a bipolar impedance between the first electrode and the second electrode; and (3) measuring a field potential at the second electrode; and
    estimating a remaining one of the (1) first and second monopolar impedances; (2) the bipolar impedance; and (3) the field potential based on the performance of the two measurements.

28. The method of claim 27, wherein the remaining one of the (1) first and second monopolar impedances; (2) the bipolar impedance; and (3) the field potential is estimated in accordance with the equation $\Phi=(I_{bp}-I_{mp1}-I_{mp2})/2$, where $\Phi$ equals the field potential, $I_{bp}$ equals the bipolar electrical impedance, $I_{mp1}$ equals the first monopolar electrical impedance, and $I_{mp2}$ equals the second monopolar electrical impedance.

* * * * *